US012114965B2

(12) United States Patent
Taniguchi et al.

(10) Patent No.: US 12,114,965 B2
(45) Date of Patent: Oct. 15, 2024

(54) CUFF COVER FOR BLOOD PRESSURE MEASUREMENT DEVICE

(71) Applicants: OMRON Corporation, Kyoto (JP); OMRON HEALTHCARE Co., Ltd., Kyoto (JP)

(72) Inventors: Minoru Taniguchi, Kyoto (JP); Masaki Harada, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 671 days.

(21) Appl. No.: 17/304,501

(22) Filed: Jun. 22, 2021

(65) Prior Publication Data

US 2021/0307627 A1    Oct. 7, 2021

Related U.S. Application Data

(63) Continuation of application No. PCT/JP2019/048038, filed on Dec. 9, 2019.

(30) Foreign Application Priority Data

Dec. 27, 2018   (JP) ................................ 2018-246187

(51) Int. Cl.
*A61B 5/021*   (2006.01)
*A61B 5/00*    (2006.01)
*A61B 5/022*   (2006.01)

(52) U.S. Cl.
CPC ...... *A61B 5/02141* (2013.01); *A61B 5/02233* (2013.01); *A61B 5/6824* (2013.01); *A61B 2560/04* (2013.01)

(58) Field of Classification Search
CPC ............ A61B 5/02141; A61B 5/02233; A61B 5/6824; A61B 2560/04
See application file for complete search history.

(56) References Cited

U.S. PATENT DOCUMENTS

| 8,652,057 B2* | 2/2014 | Vivenzio | A61B 5/02233 600/490 |
| 2011/0112412 A1* | 5/2011 | Sano | A61B 5/02233 600/499 |
| 2016/0029910 A1* | 2/2016 | Taniguchi | A61B 5/022 600/499 |

FOREIGN PATENT DOCUMENTS

| JP | H09-238910 A | 9/1997 |
| JP | 3139521 U | 2/2008 |

(Continued)

OTHER PUBLICATIONS

International Preliminary Report on Patentability and Written Opinion of the International Searching Authority issued Jul. 8, 2021 in International (PCT) Patent Application No. PCT/JP2019/048038.

*Primary Examiner* — Devin B Henson
(74) *Attorney, Agent, or Firm* — Wenderoth, Lind & Ponack, L.L.P.

(57) ABSTRACT

Provided is a cuff cover for a blood pressure measurement device including a bag body having a stretchable bag-like shape with a length that allows a cuff structure and a curler curving and following along a shape of the wrist to be disposed inside the bag body, a first hole portion extending in a longitudinal direction of the bag body and provided at a portion of the bag body facing the outer circumferential surface of the curler, the first hole portion being configured to allow the curler provided with the cuff structure to be inserted by elongating the bag body, and a second hole portion formed in a shape allowing the power feeding terminal to be exposed, the second hole portion being provided at a portion of the bag body facing the power feeding terminal provided on the outer circumferential surface of the curler.

4 Claims, 31 Drawing Sheets

(56) References Cited

FOREIGN PATENT DOCUMENTS

| | | |
|---|---|---|
| JP | 2010-36048 A | 2/2010 |
| JP | 1615126 S | 10/2018 |
| JP | 1640133 S | 9/2019 |

\* cited by examiner

[FIG. 1]
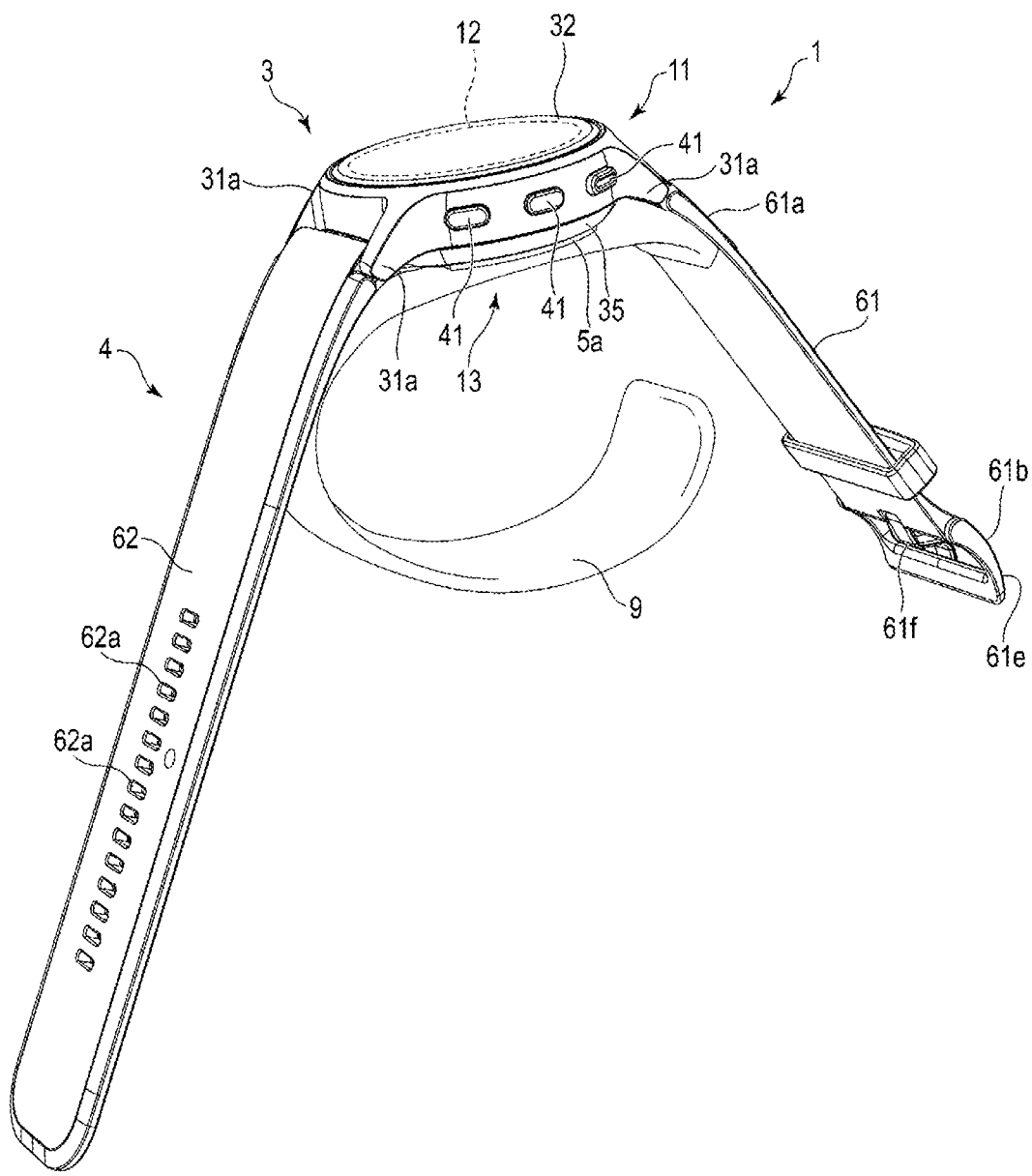

[FIG. 2]
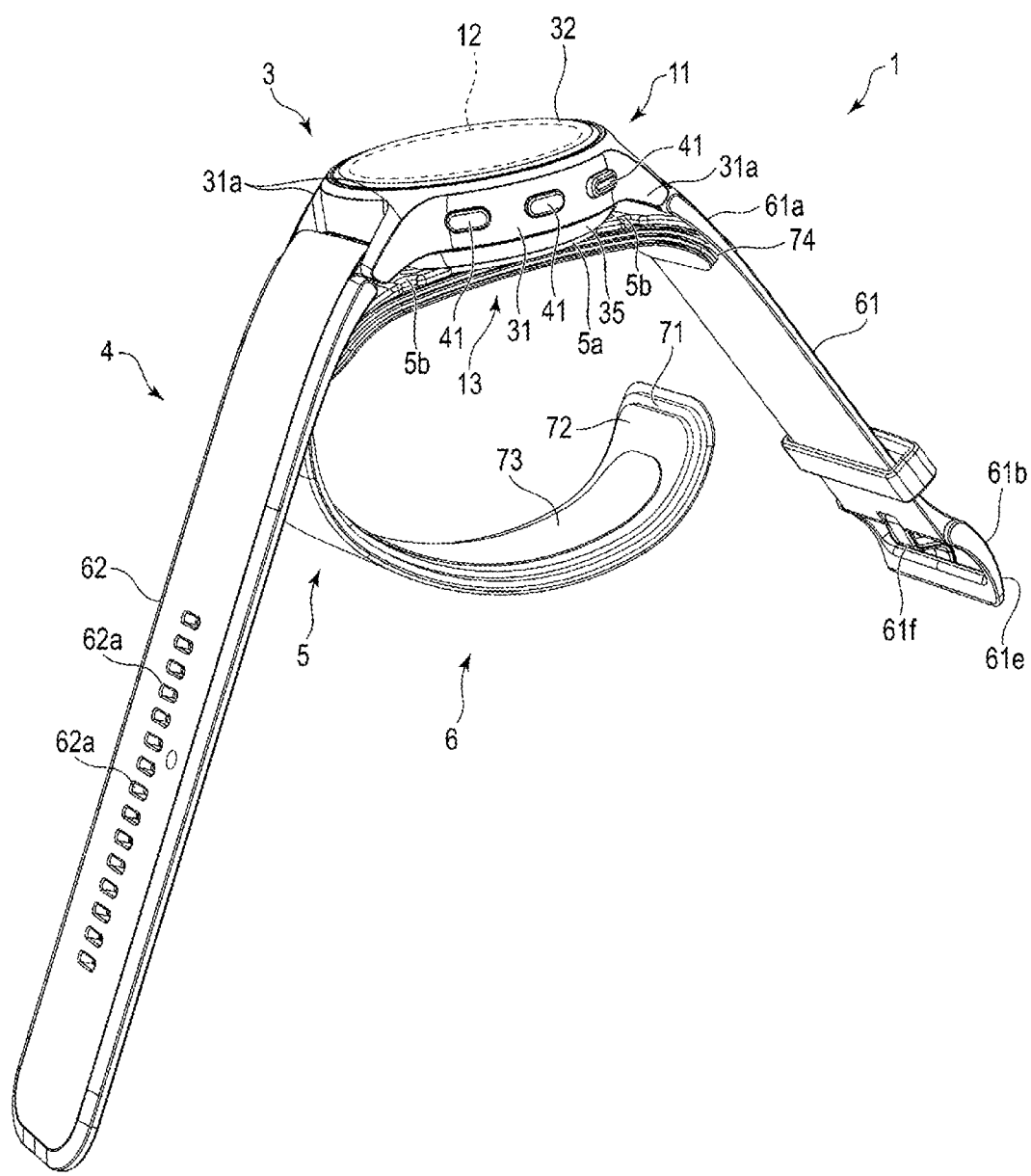

[FIG. 3]
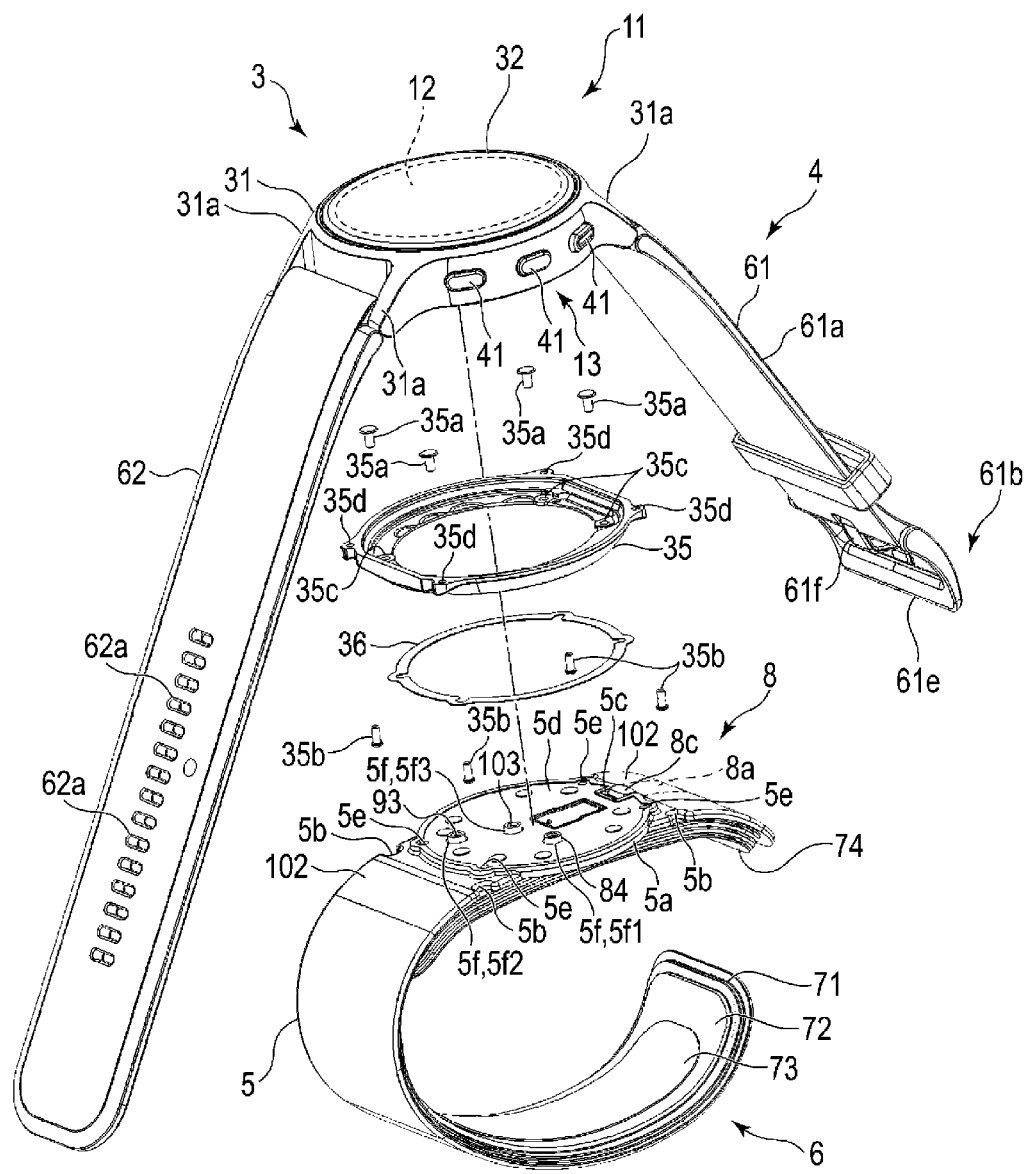

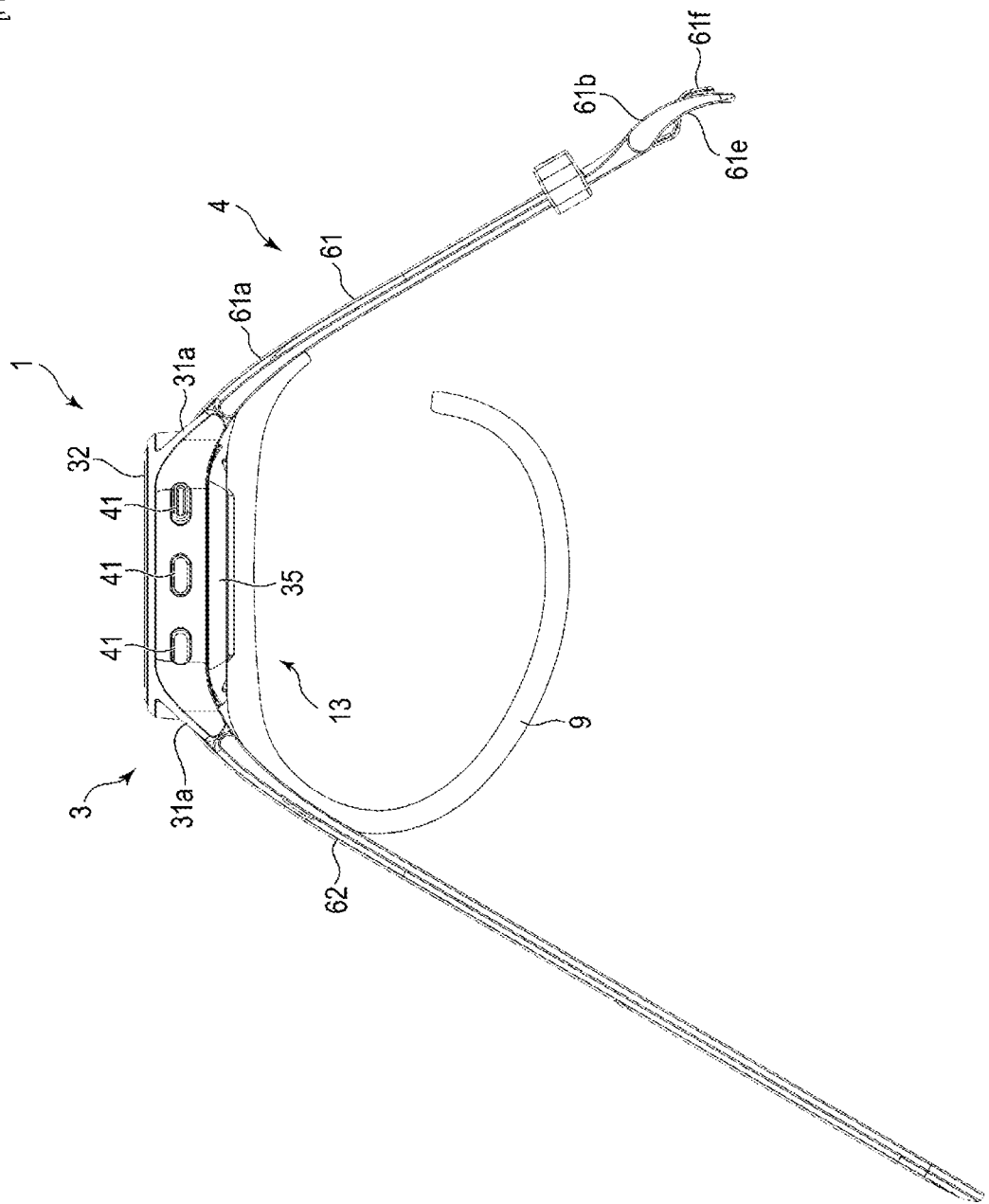
[FIG. 4]

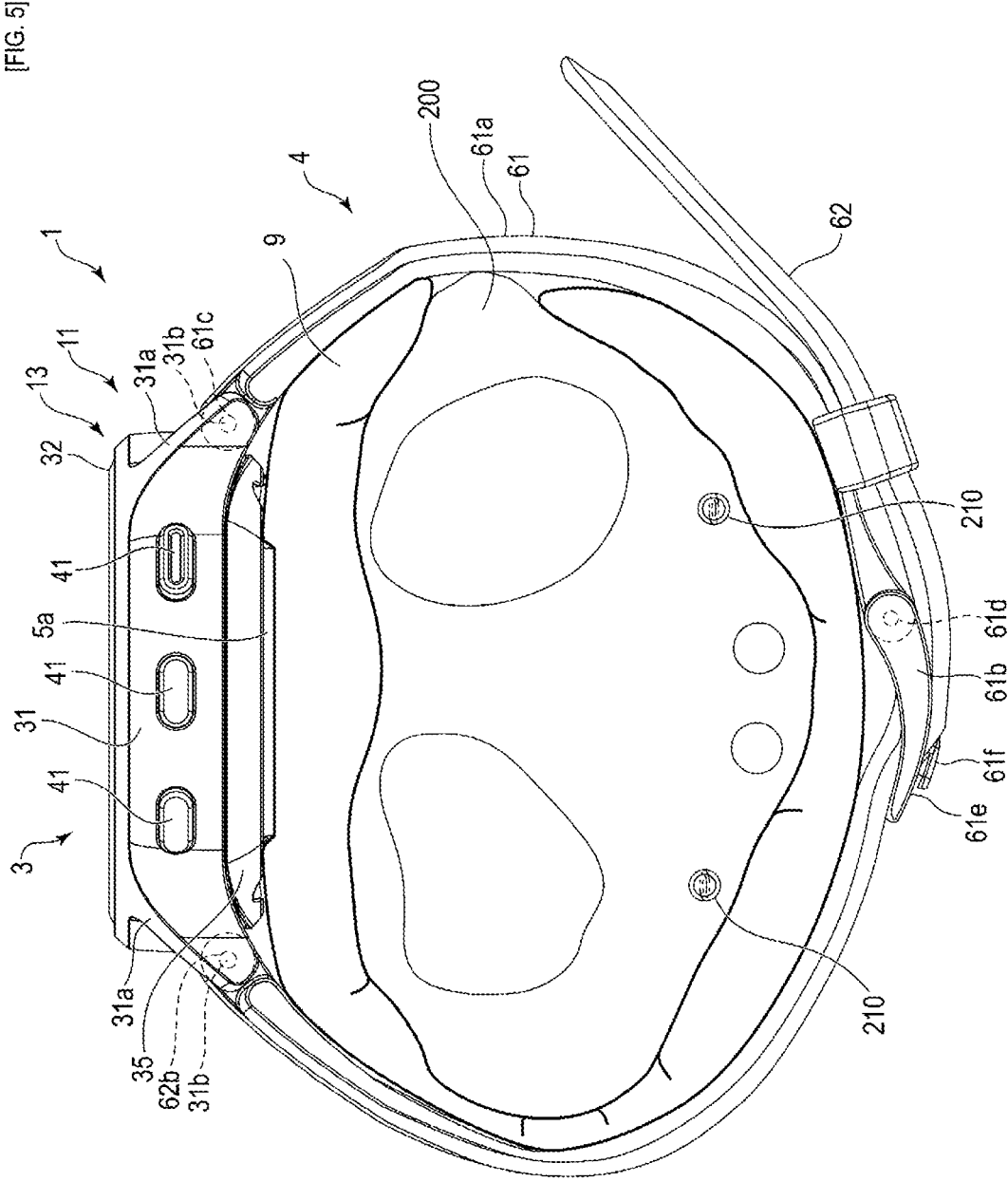

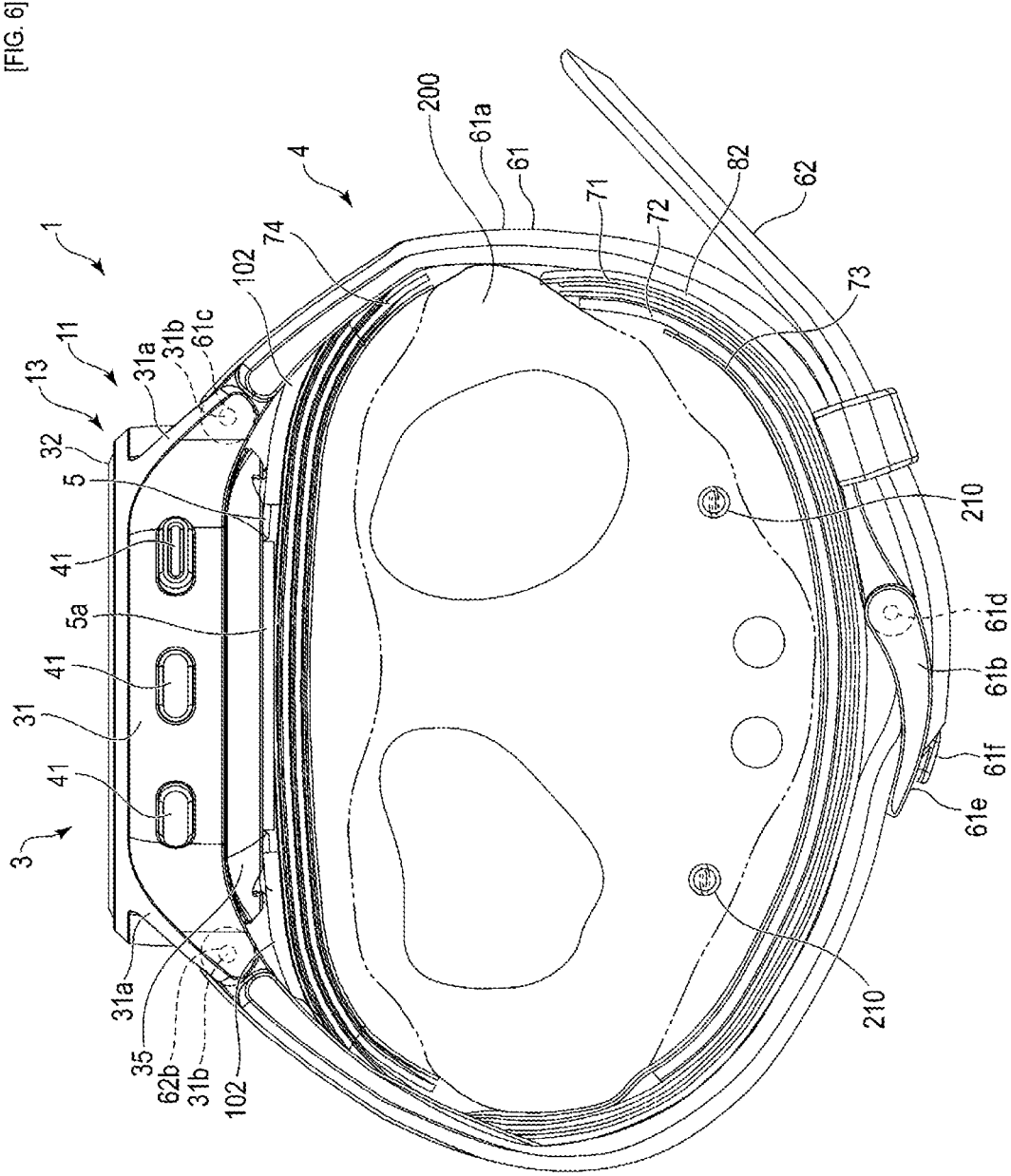
[FIG. 6]

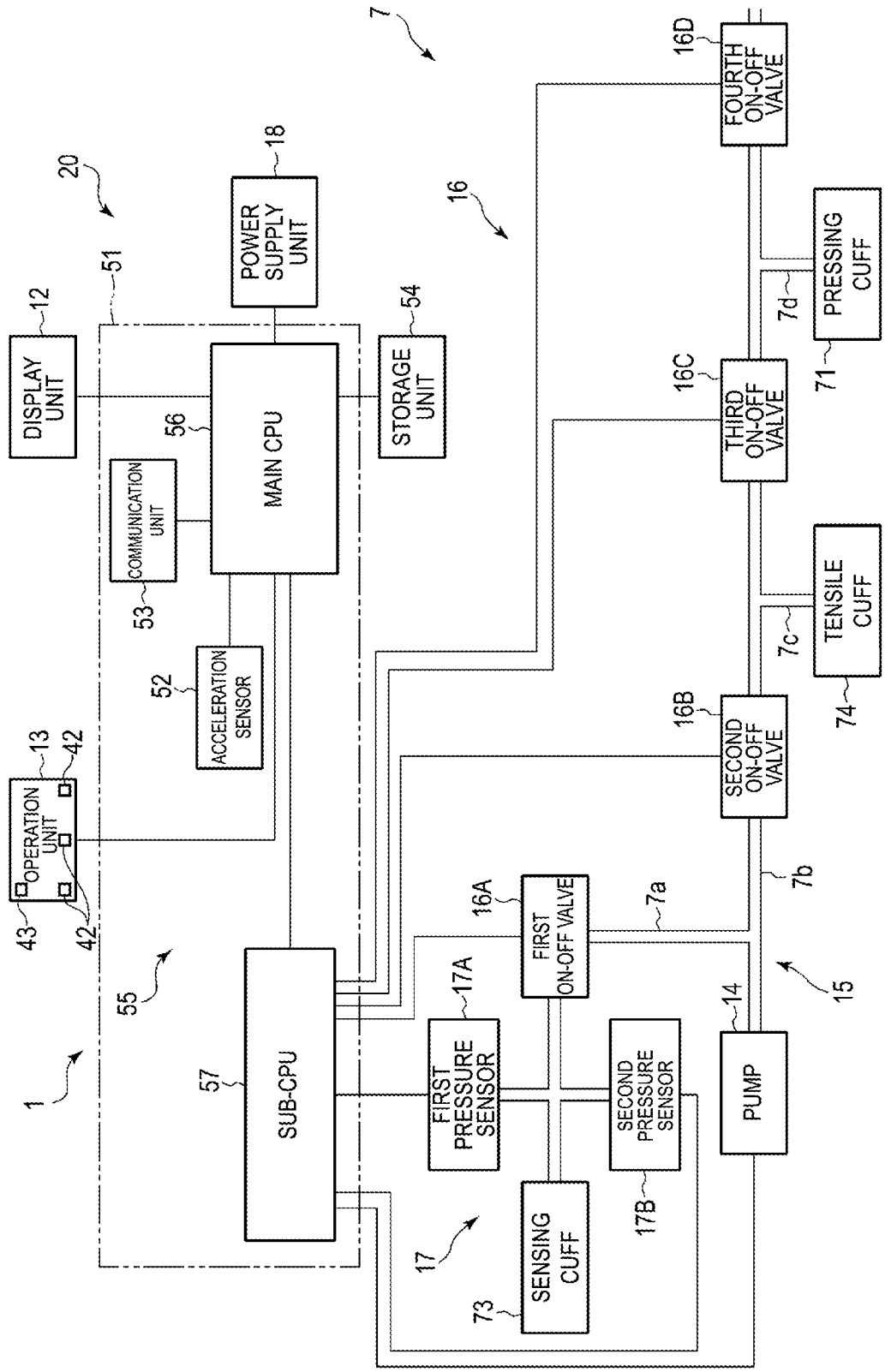
[FIG. 7]

[FIG. 8]
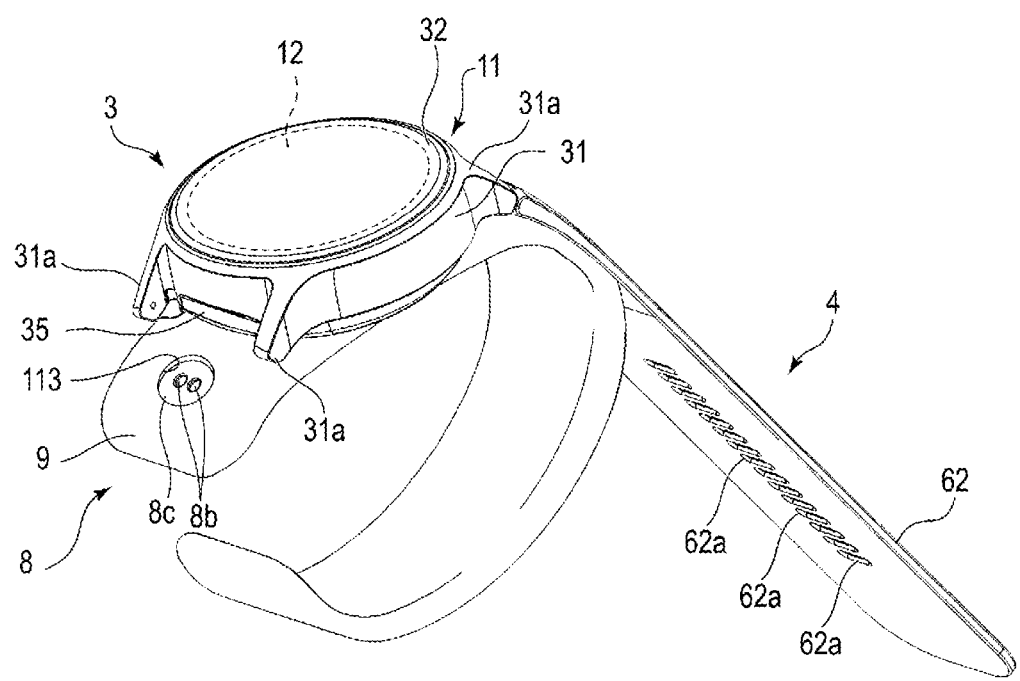

[FIG. 9]
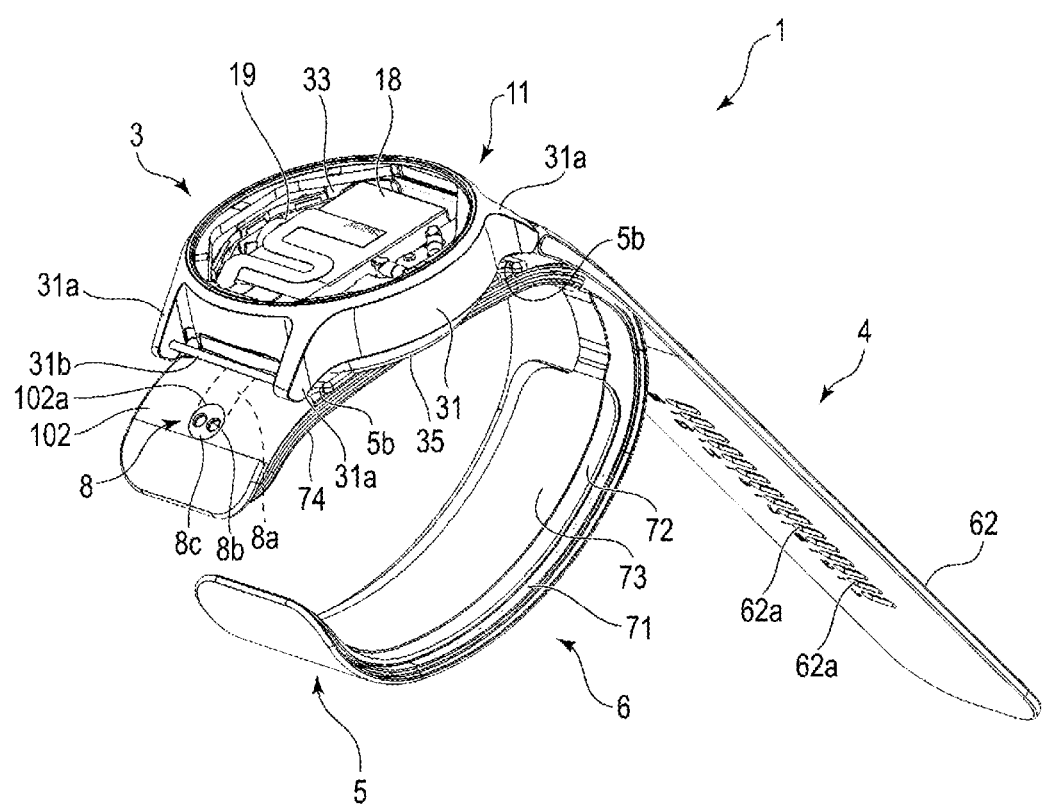

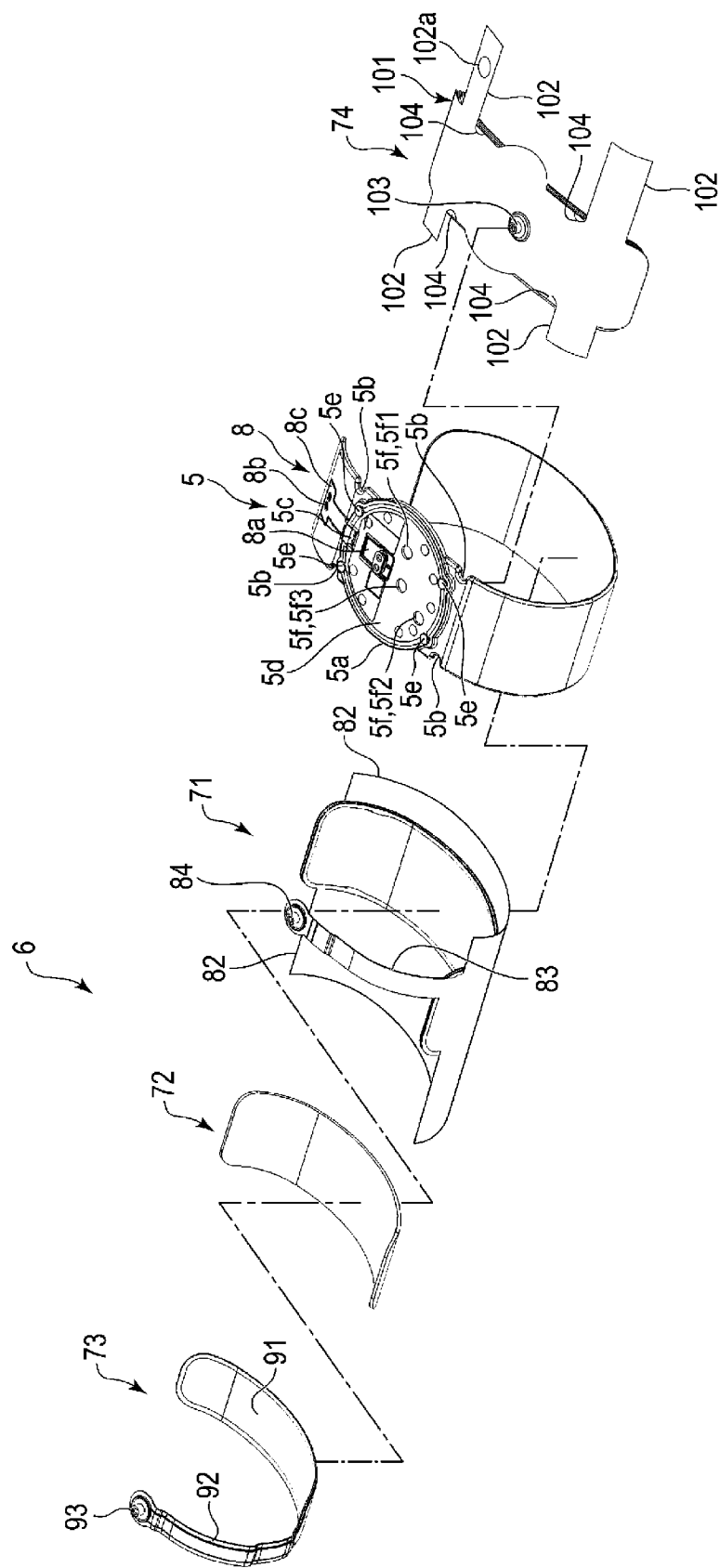
[FIG. 10]

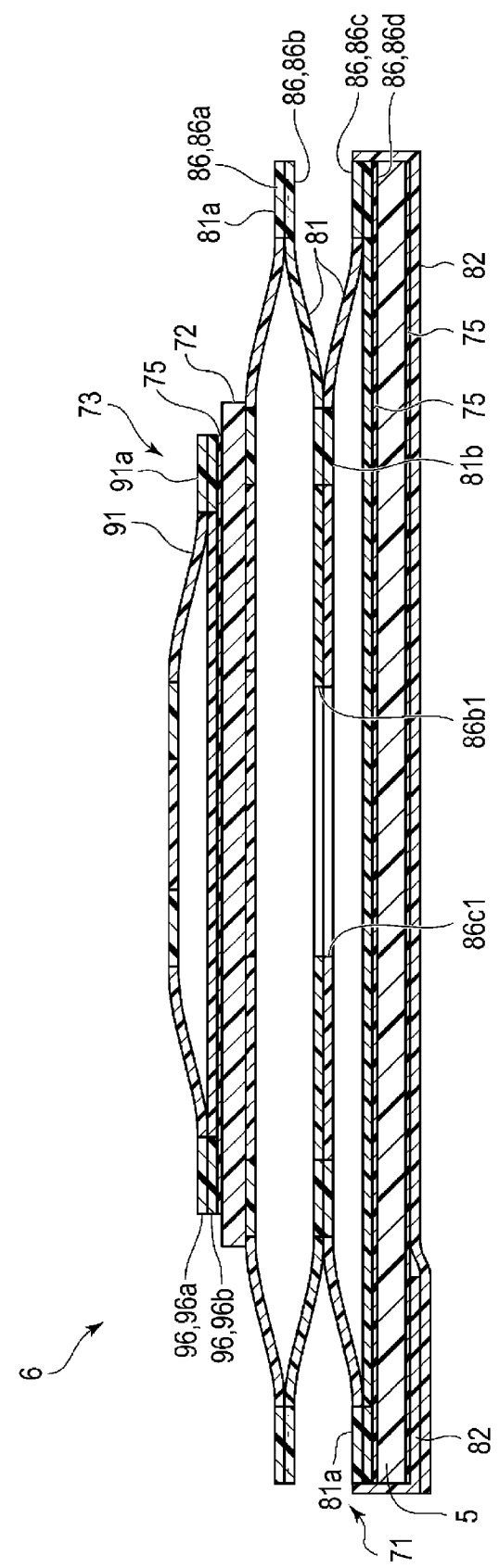
[FIG. 11]

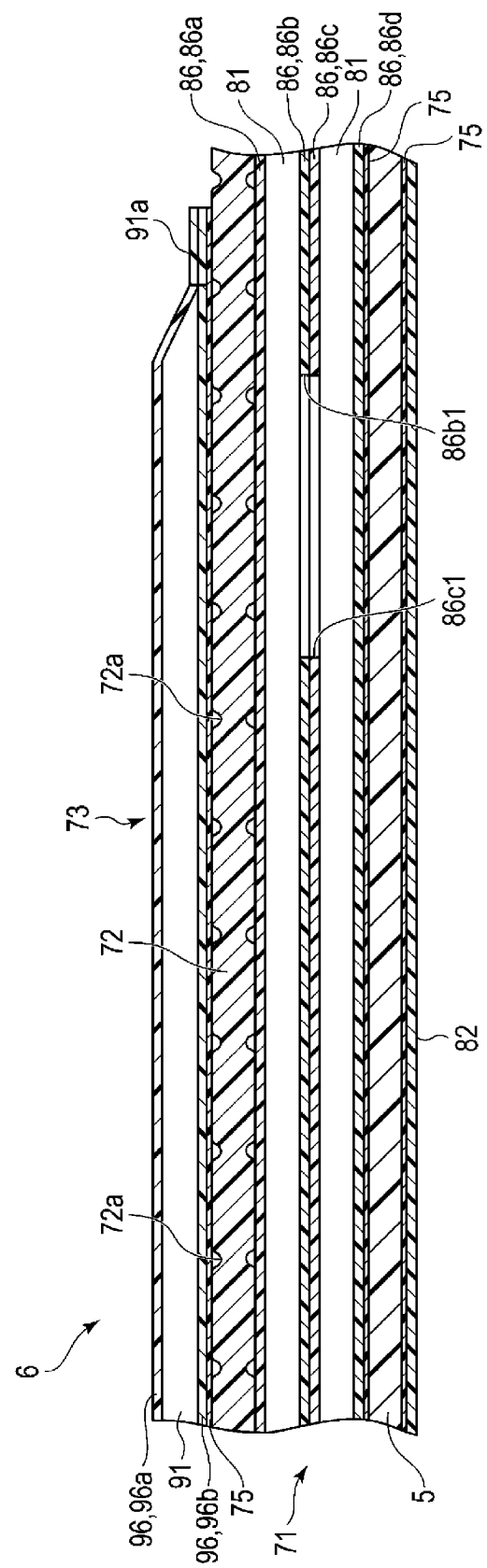

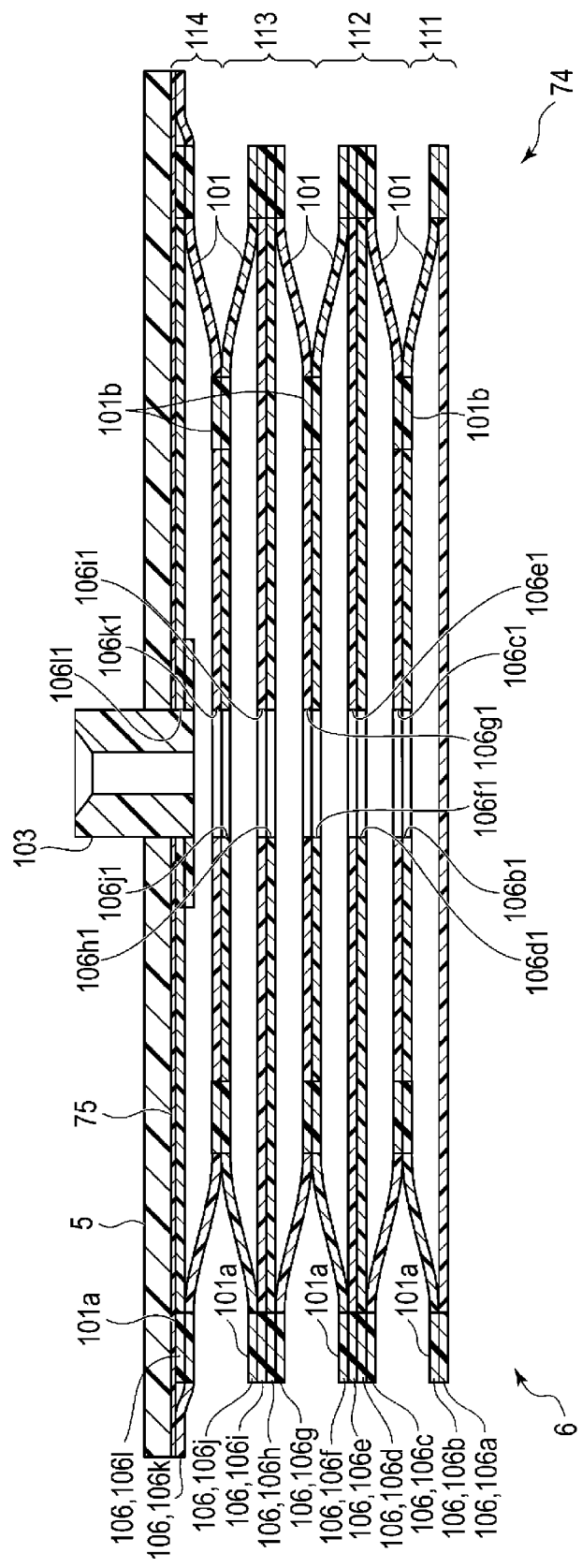
[FIG. 13]

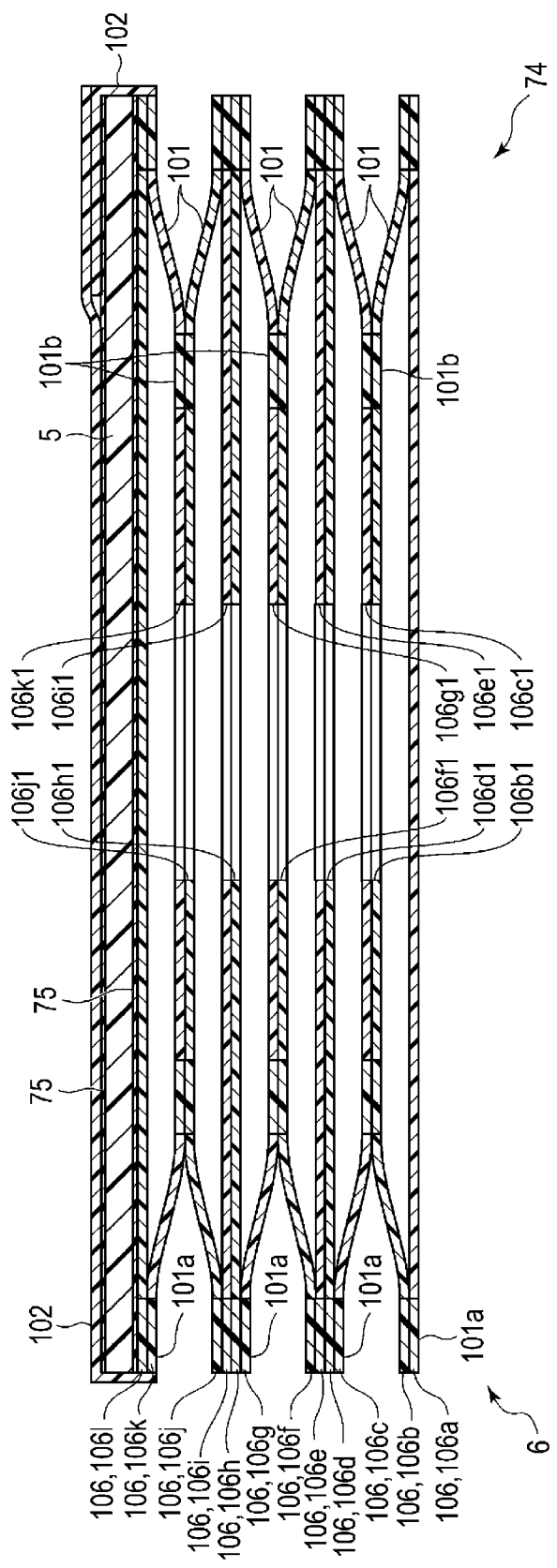

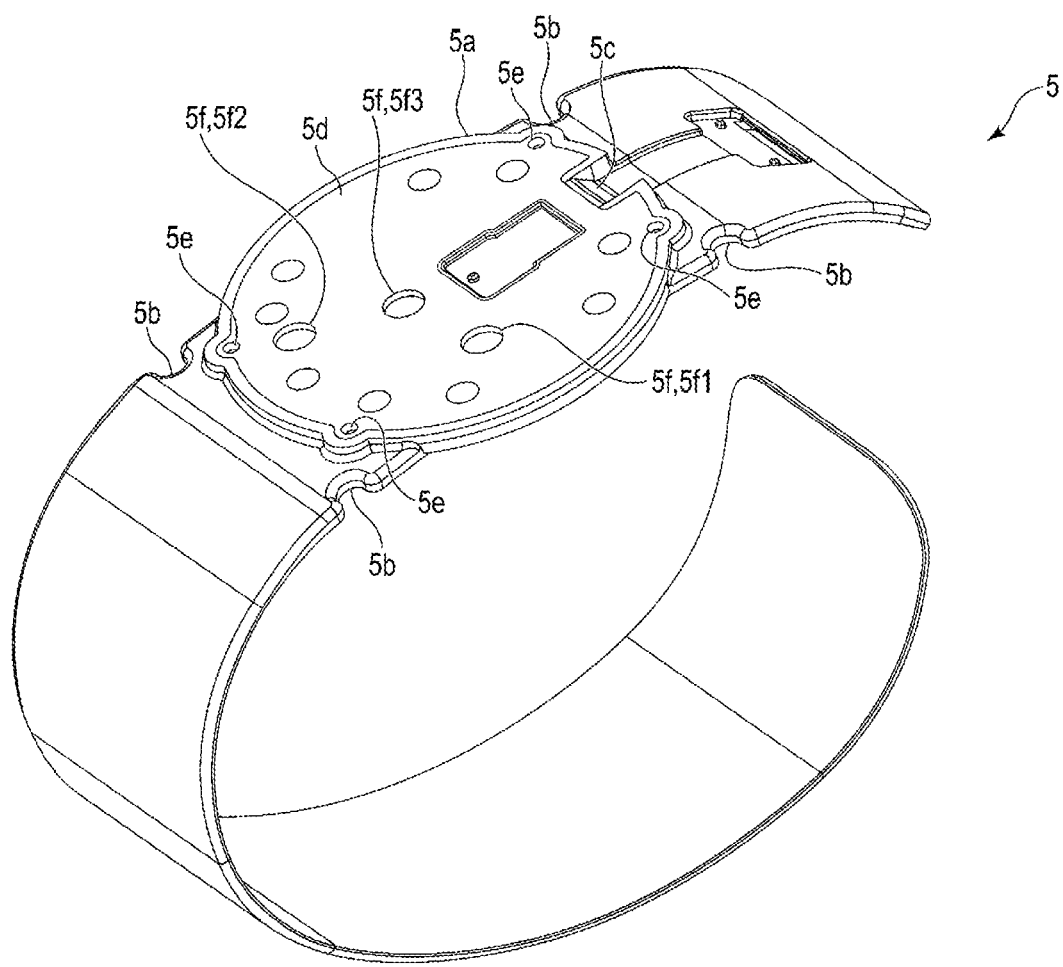

[FIG. 16]
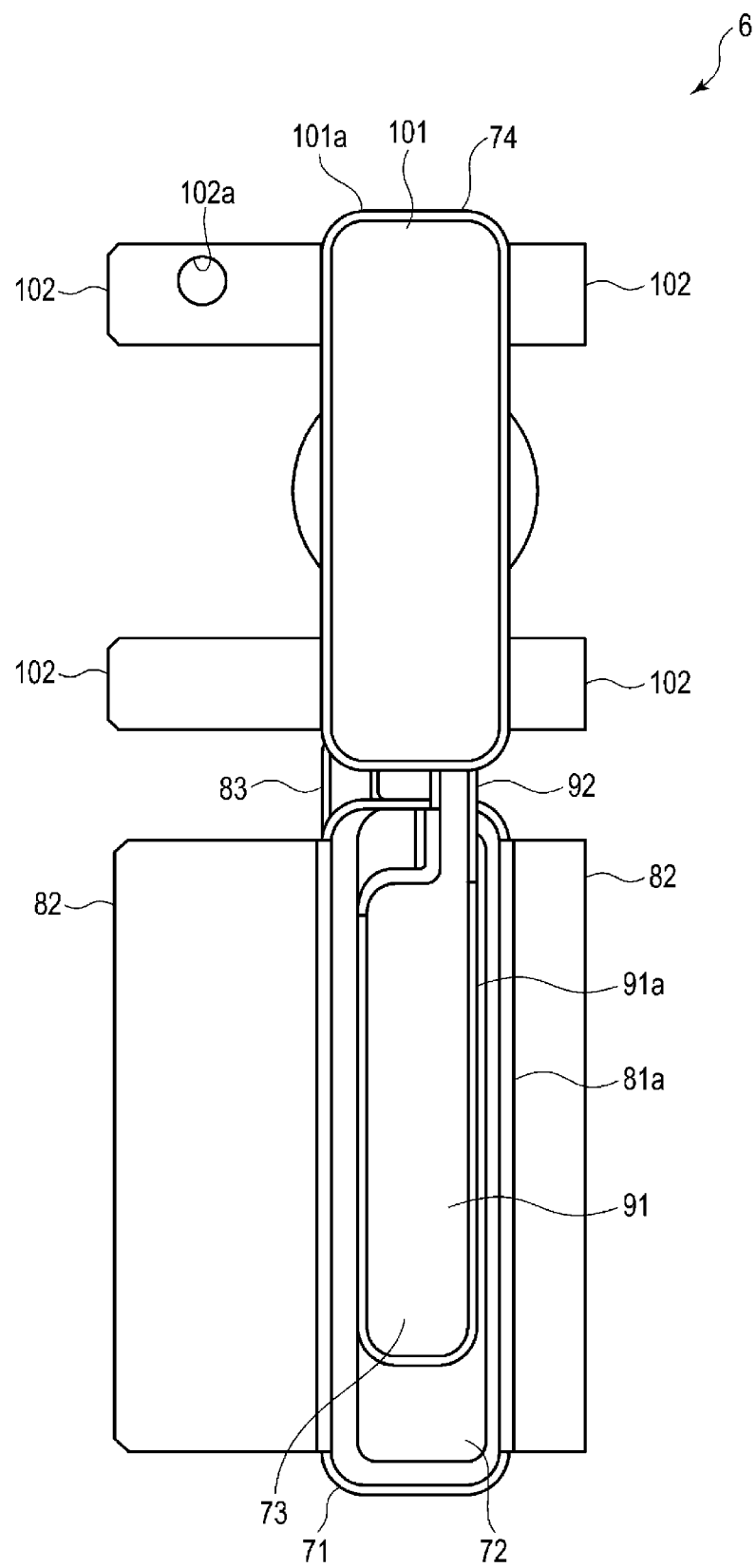

[FIG. 17]
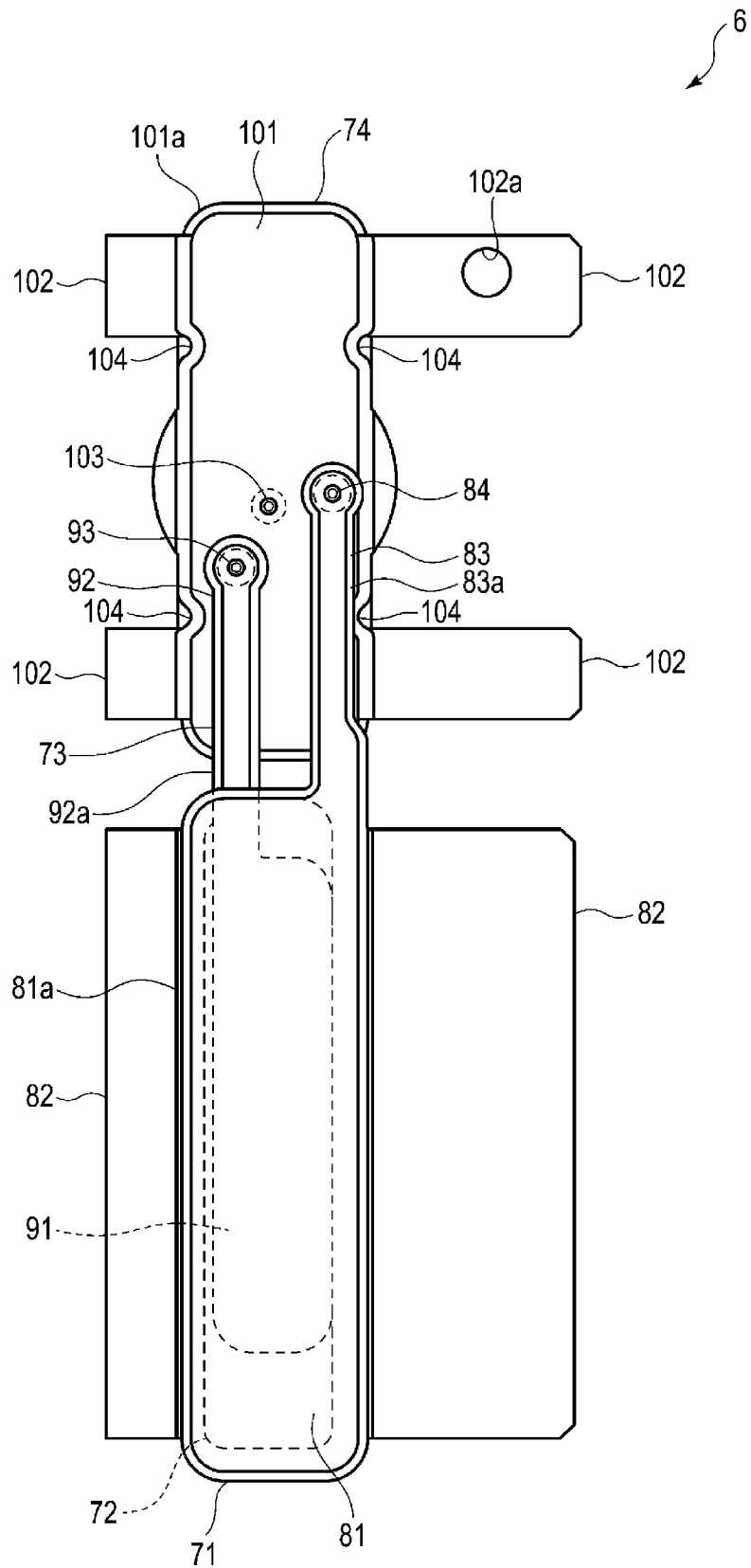

[FIG. 18]
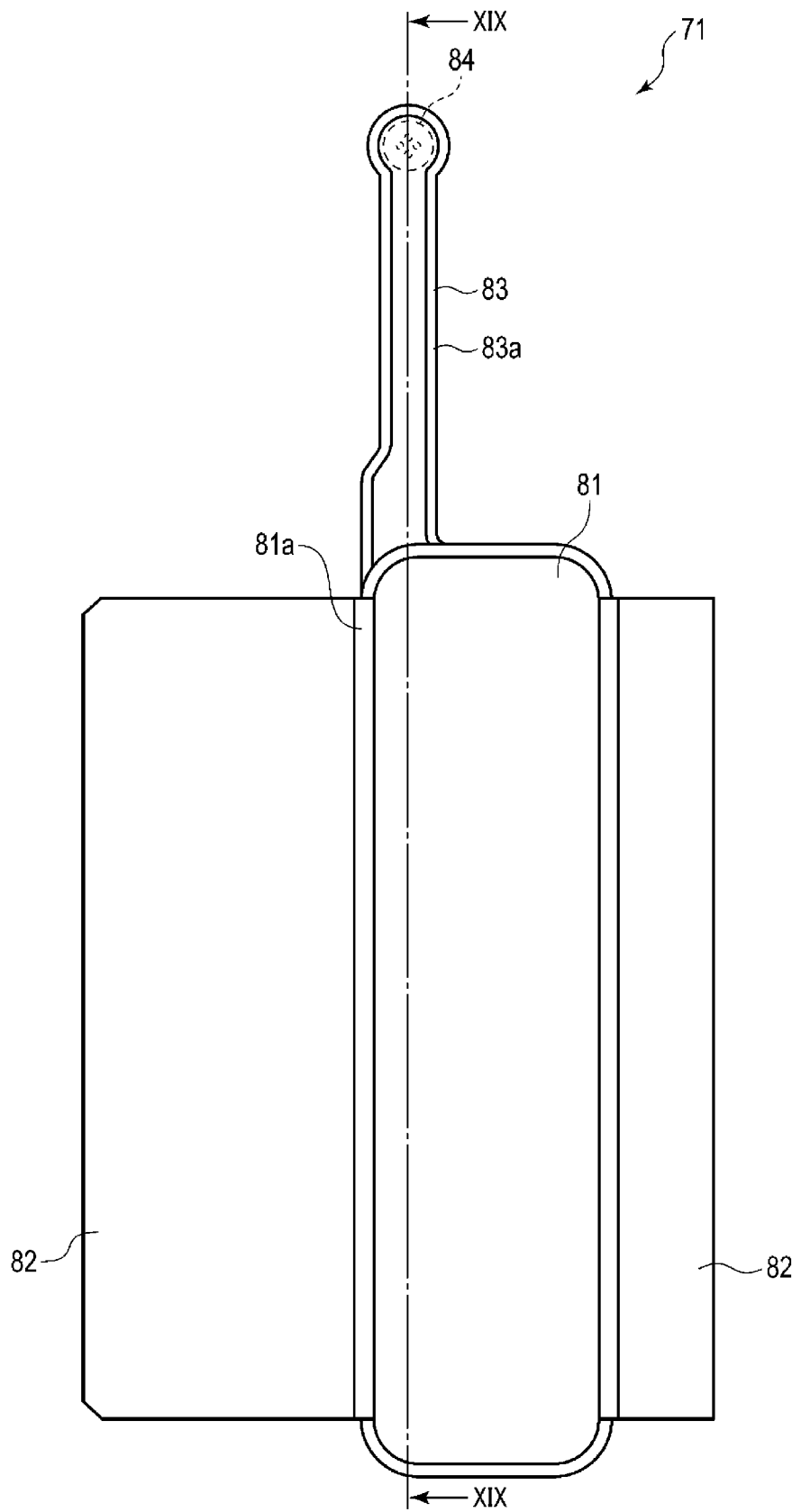

[FIG. 19]
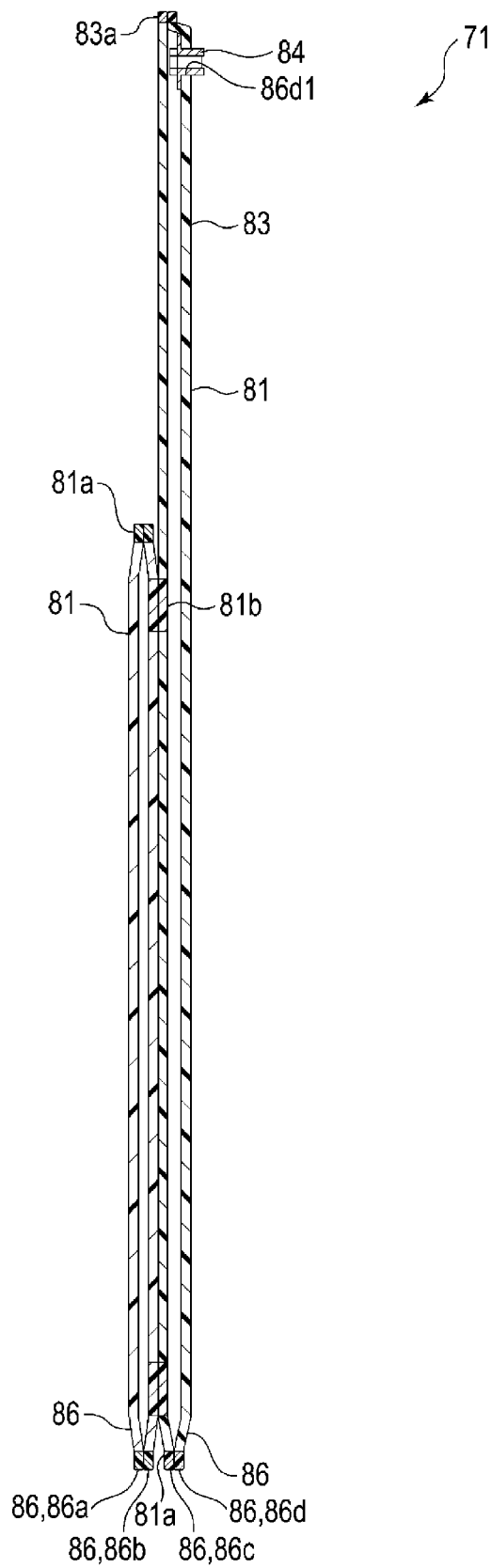

[FIG. 20]
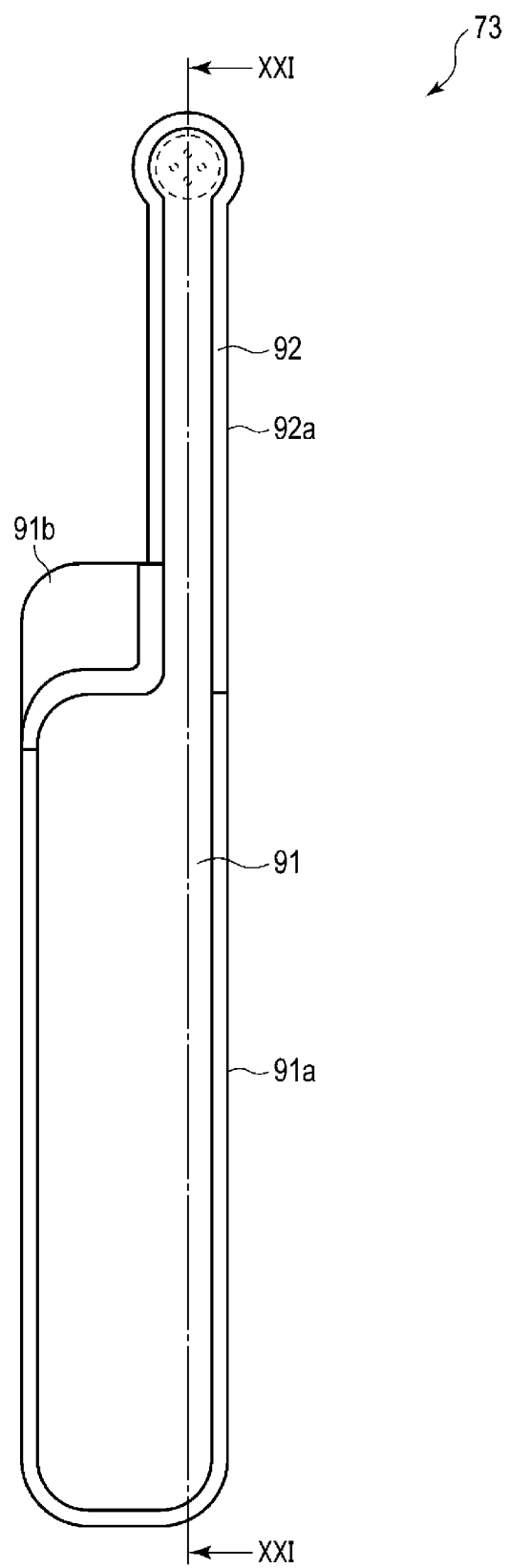

[FIG. 21]
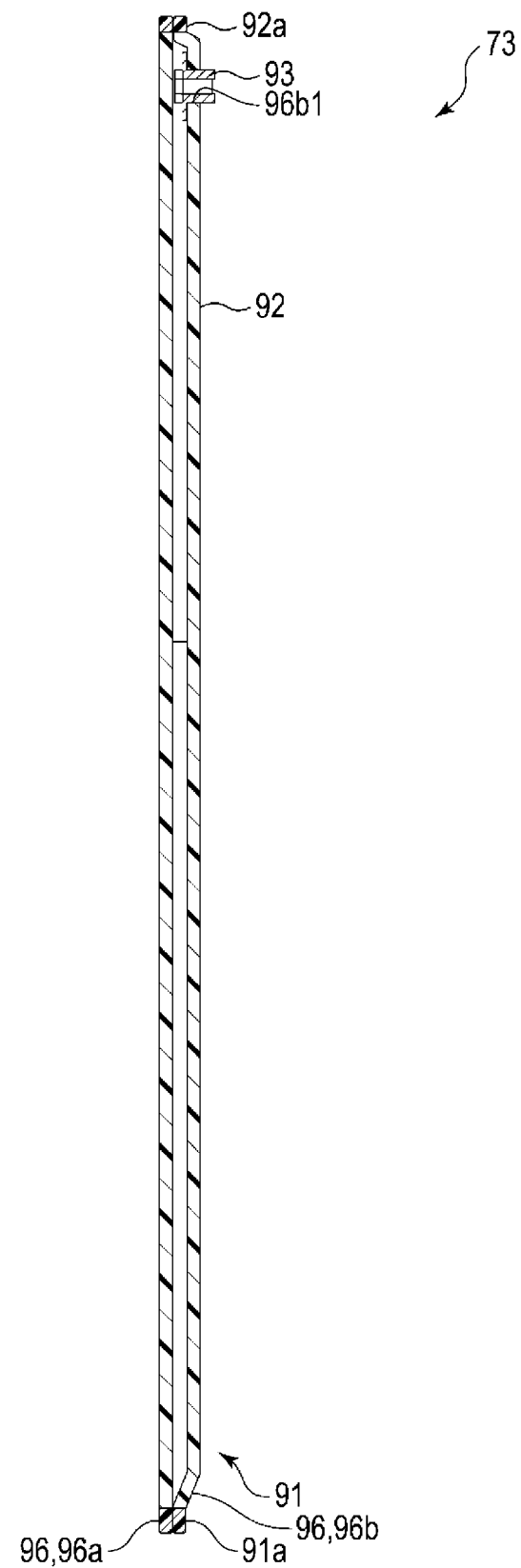

[FIG. 22]
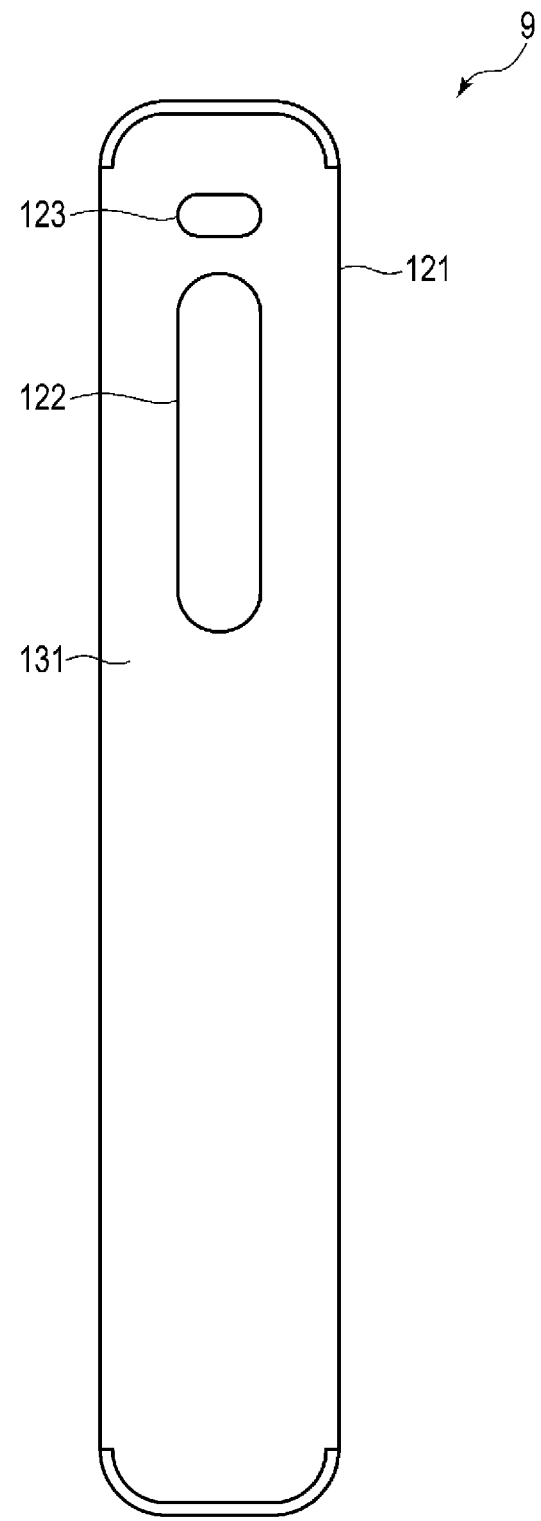

[FIG. 23]
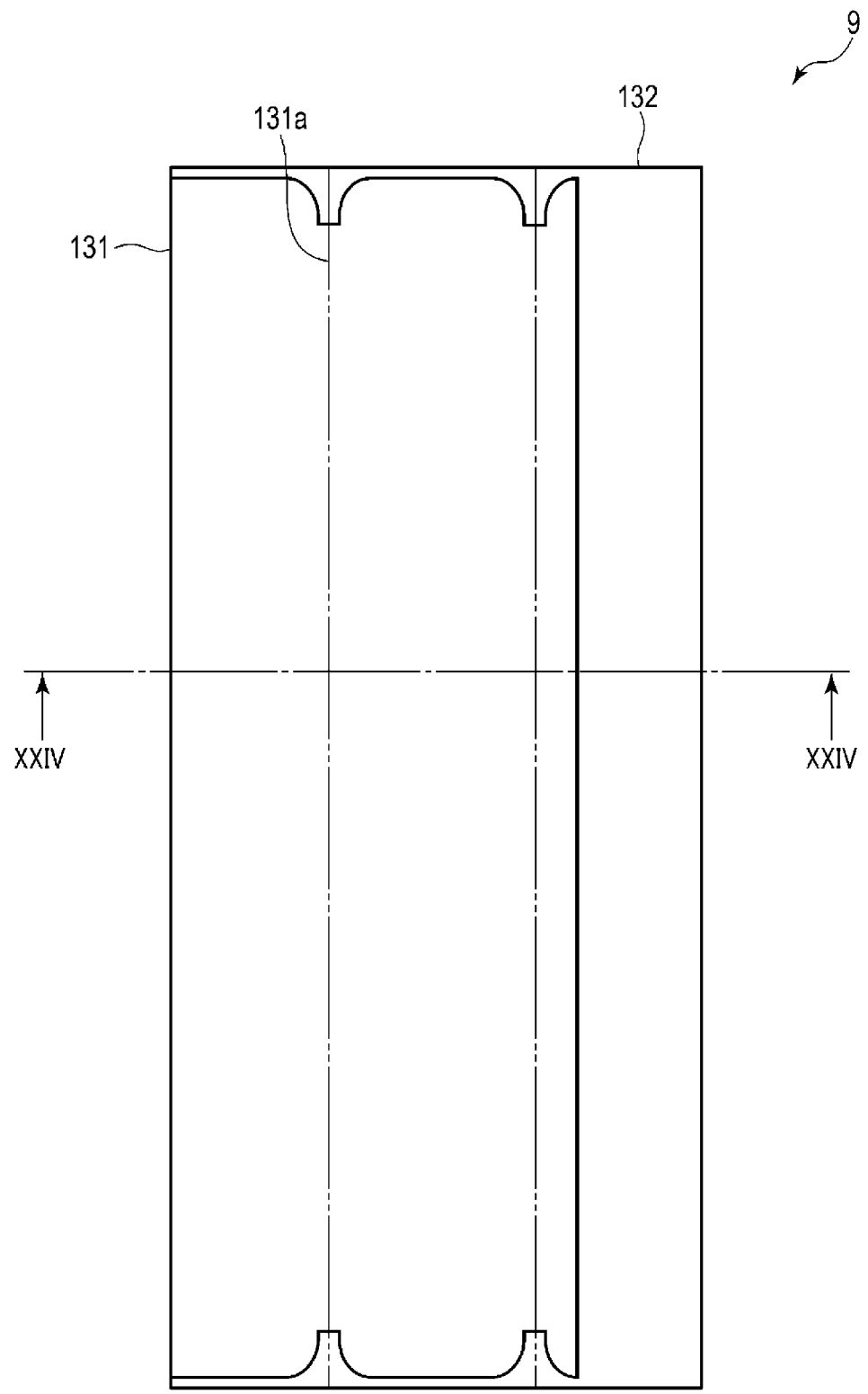

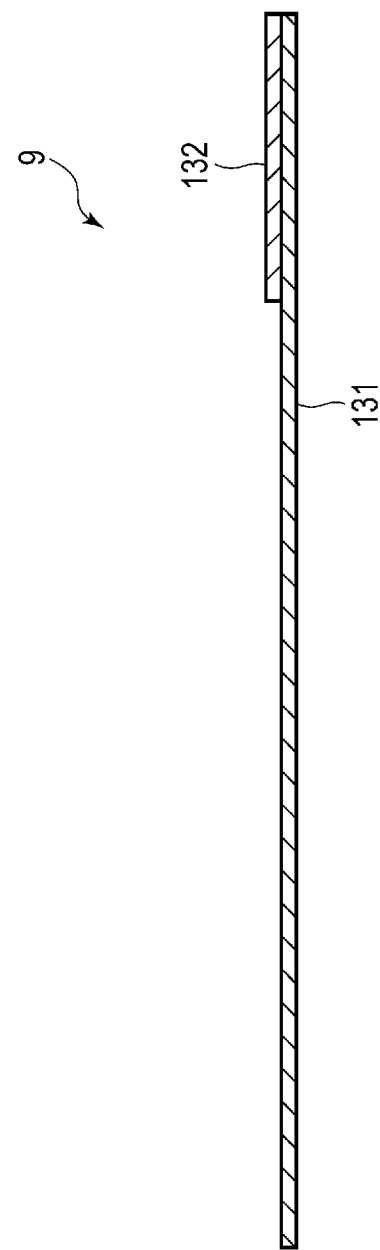

[FIG. 25]
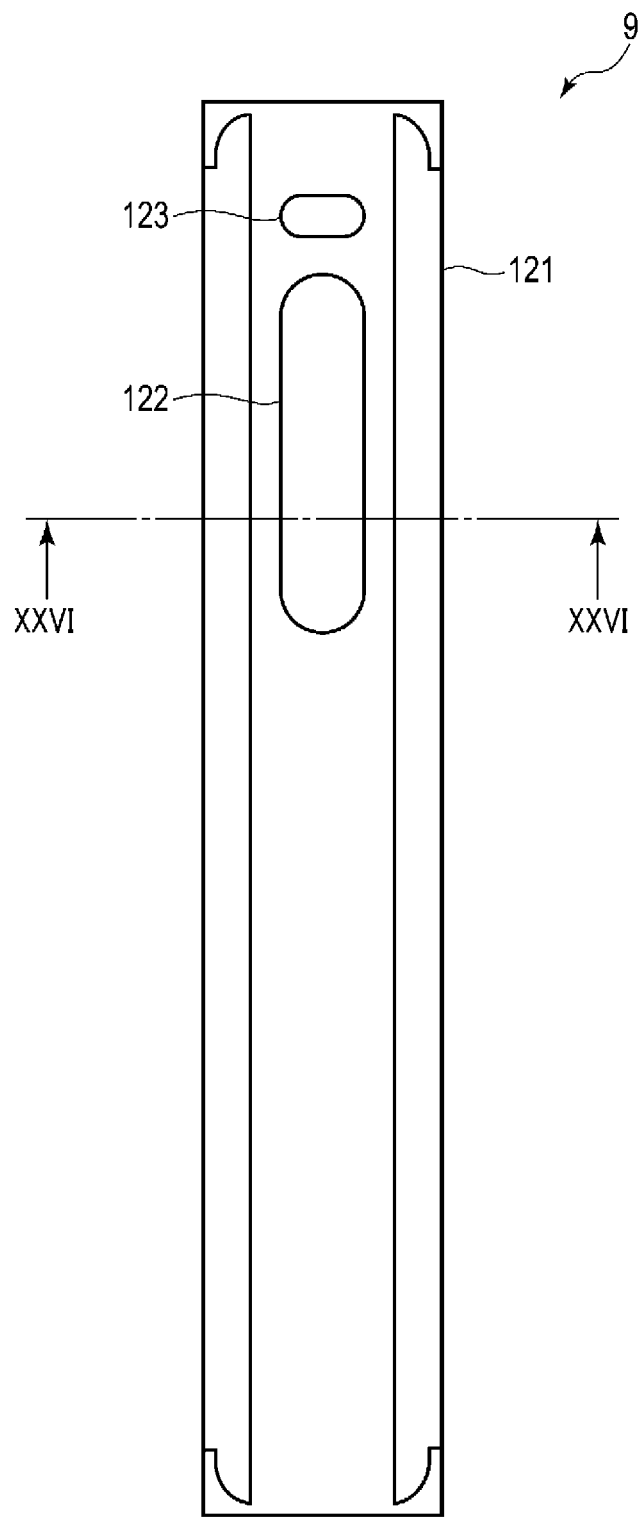

[FIG. 26]
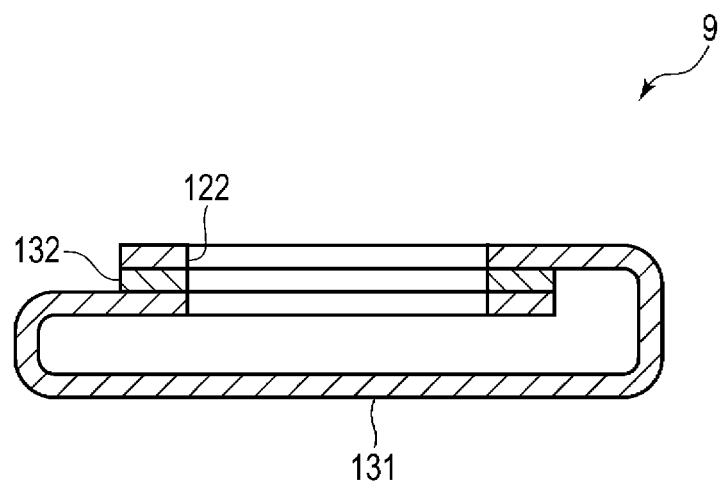

[FIG. 27]
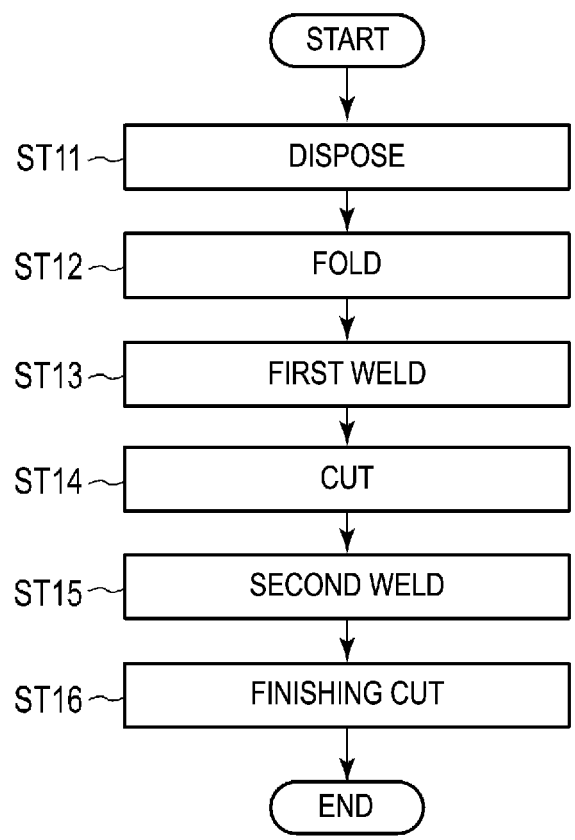

[FIG. 28]
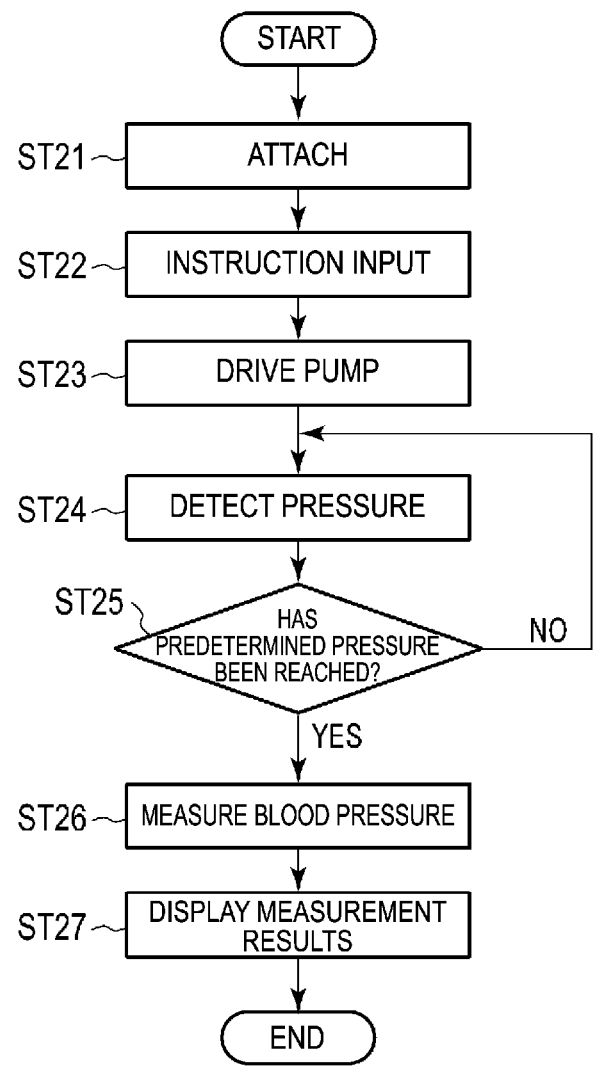

[FIG. 29]
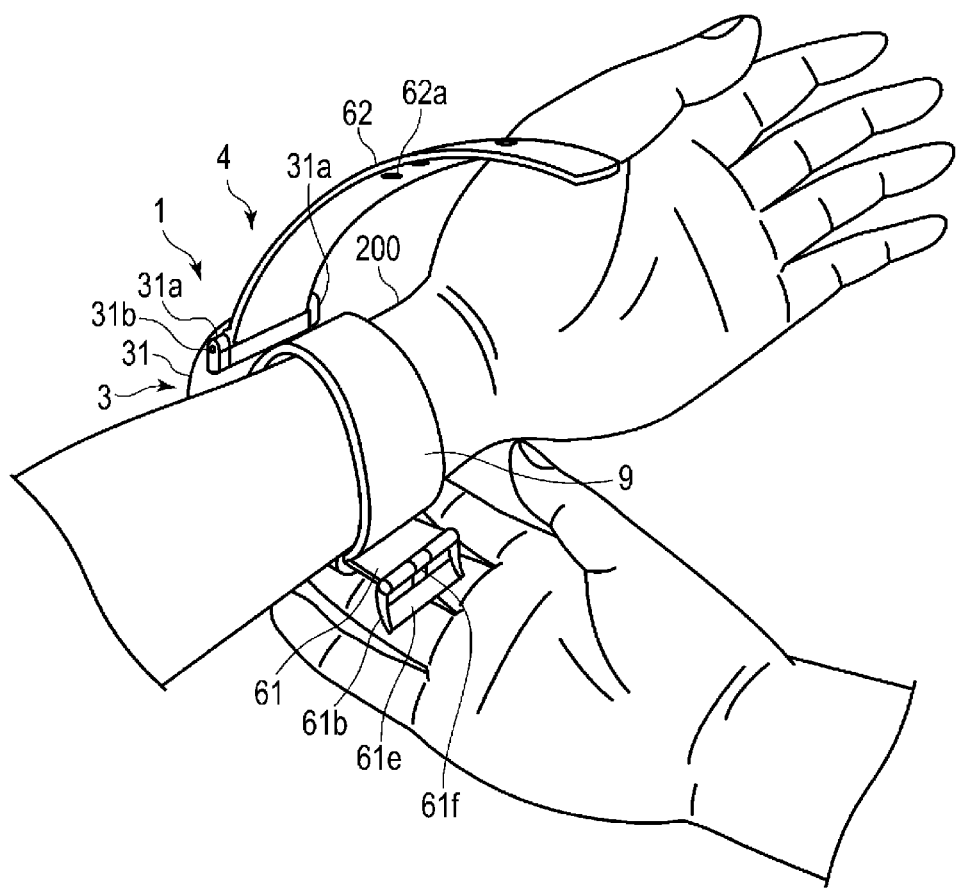

[FIG. 30]
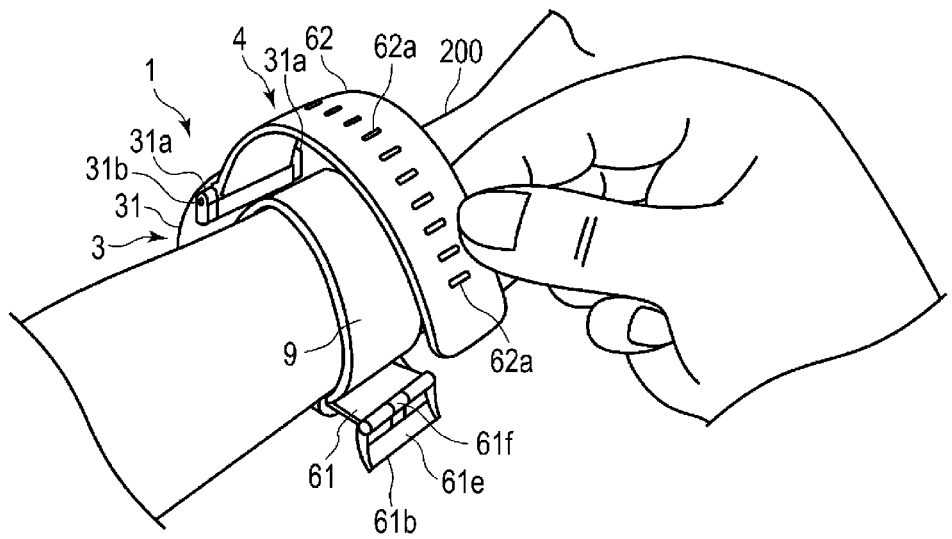
[FIG. 31]
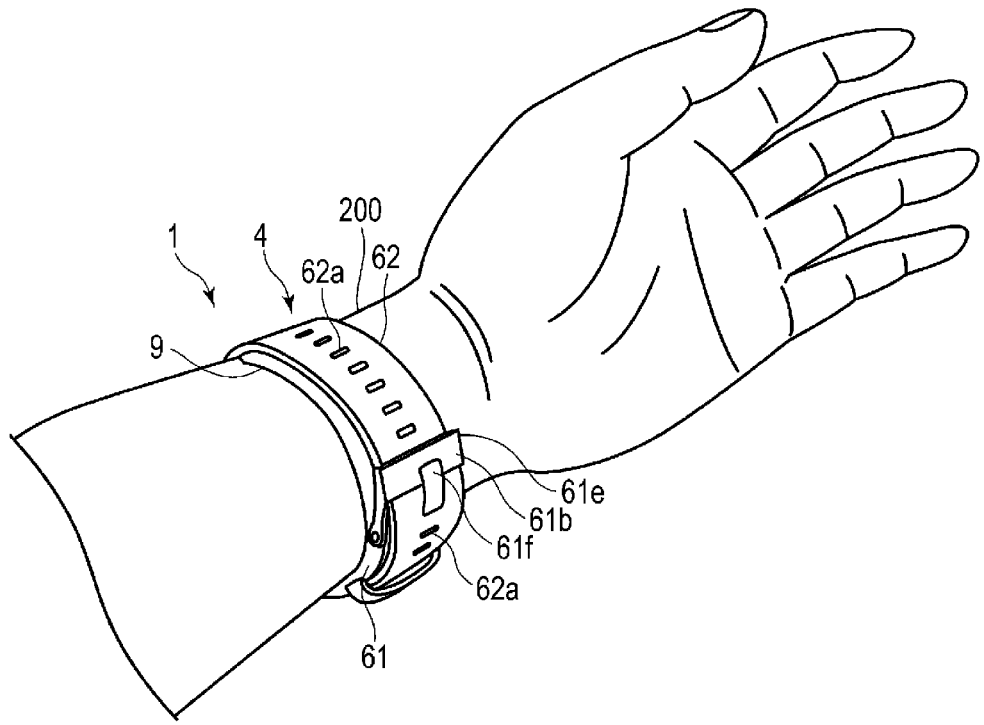

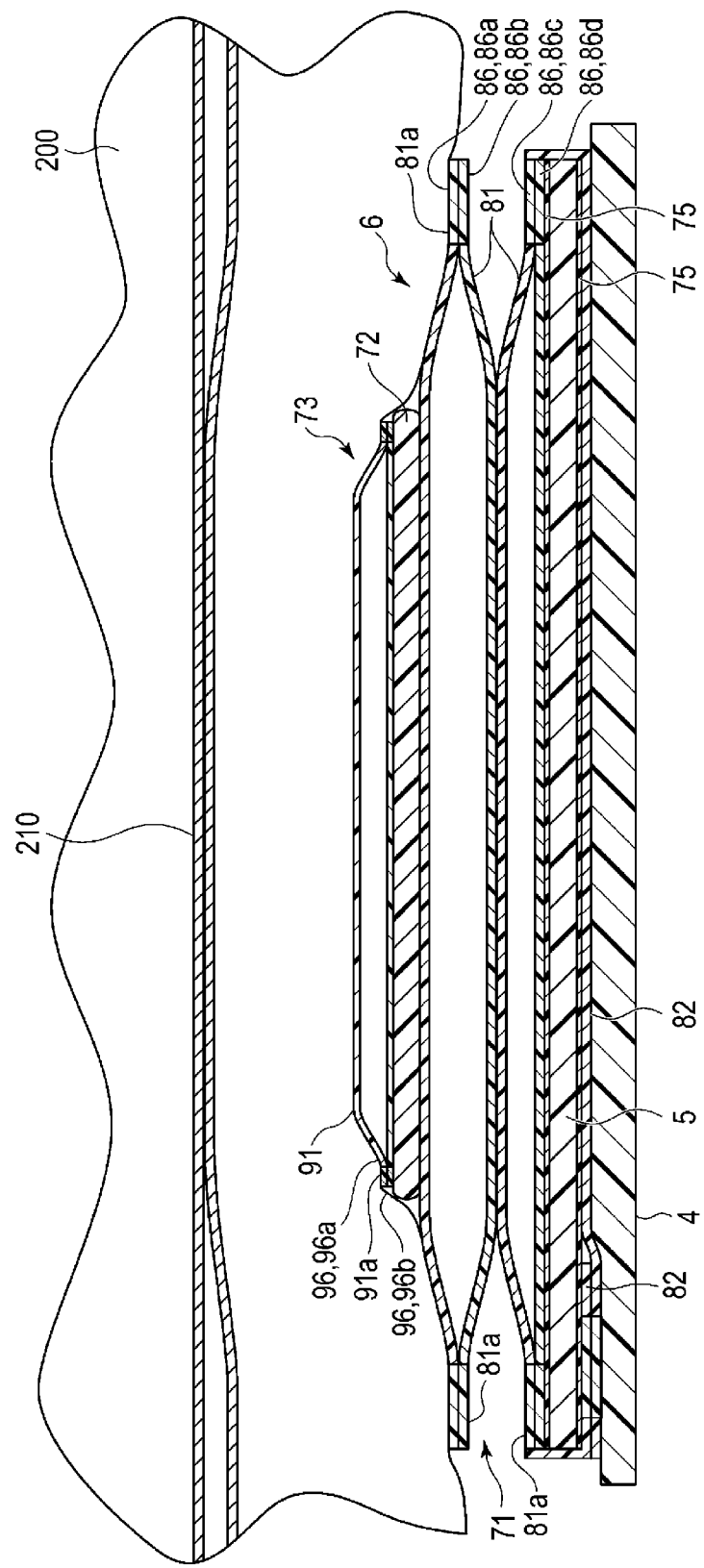
[FIG. 32]

CUFF COVER FOR BLOOD PRESSURE MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2019/048038, filed Dec. 9, 2019, which application claims priority to Japan Patent Application No. 2018-246187, filed Dec. 27, 2018, which applications are incorporated herein by reference in their entireties.

TECHNICAL FIELD

The present invention relates to a cuff cover for a blood pressure measurement device for measuring blood pressure.

BACKGROUND ART

In recent years, blood pressure measurement devices for measuring blood pressure are being used to monitor health status at home, as well as in medical facilities. A blood pressure measurement device detects vibration of the artery wall to measure blood pressure by, for example, inflating and contracting a cuff wrapped around the upper arm or the wrist of a living body and detecting the pressure of the cuff using a pressure sensor.

As such a blood pressure measurement device, for example, a so-called integral type is known in which a cuff is integrated with a device body supplying a fluid to the cuff. Such blood pressure measurement devices have the problem that when a wrinkle, fold, or the like is generated in the cuff, the accuracy of the measured blood pressure measurement result is reduced. There is also a demand for blood pressure measurement devices in which the cuff expands in the direction in which the blood vessels are occluded and the cuff comes into close contact with the wrist when the cuff is inflated. In regards to this, as described in JP H09-238910 A, for example, a known blood pressure measurement device uses a curler to bring an inflated cuff into close contact with the wrist. In such blood pressure measurement devices, a configuration in which a cuff and a curler is covered by a protective cloth is known.

Recently, wearable devices attached to the wrist have been proposed, and there has been a demand for further miniaturization of blood pressure measurement devices. In the case where the blood pressure measurement device is used as a wearable device, for example, a configuration is conceivable in which a cuff structure provided with a plurality of cuffs is provided, the width of the curler and the cuff structure is narrowed, and the curler is tightened by a belt provided on the device body.

CITATION LIST

Patent Literature

Patent Document 1: JP H09-238910 A

SUMMARY OF INVENTION

Technical Problem

The blood pressure measurement device of the wearable device described above is expected to be used in an attached state on the wrist during daily life. However, when the cuff structure is directly in contact with the wrist, because the cuff structure is constituted by a sheet member of resin material, this leads to the problem that the site where the cuff structure comes into contact becomes stuffy. In addition, when attaching on the wrist during daily life, there is also a problem in that the curler and the cuff structure become dirty. Thus, while it is conceivable to cover the curler and the cuff structure with a cover, the device is often worn on the wrist for long periods of time, and thus the cover needs to be frequently replaced. Thus, there is a demand for a cover that is easily replaced.

Additionally, in a case where providing of the cover hinders the expansion of the cuff structure, the measurement accuracy is decreased. In particular, when the blood pressure measurement device is used as a wearable device, the effect of inhibiting the expansion of the cuff on the measurement accuracy is greater than known blood pressure measurement devices because narrowing the width of the cuff is required.

Thus, an object of the present invention is to provide a cuff cover for a blood pressure measurement device that can easily cover the cuff structure without reducing the measurement accuracy of the blood pressure measurement device.

Solution to Problem

According to an aspect, a cuff cover for a blood pressure measurement device attachable to the wrist is provided which includes, a bag body having a stretchable bag-like shape long in one direction with a length that allows a cuff structure and a curler curving and following along a shape of the wrist to be disposed inside the bag body, the cuff structure being provided on an inner circumferential surface of the curler, a device body being disposed on a portion of an outer circumferential surface of the curler, and a power feeding terminal being provided at a position on the outer circumferential surface of the curler adjacent to the device body, a first hole portion extending in a longitudinal direction of the bag body and provided at a portion of the bag body facing the outer circumferential surface of the curler, the device body being configured to be disposed at the portion, the first hole portion being configured to allow the curler provided with the cuff structure to be inserted by elongating the bag body, and a second hole portion formed in a shape allowing the power feeding terminal to be exposed, the second hold portion being provided at a portion of the bag body facing the power feeding terminal provided on the outer circumferential surface of the curler.

Here, the cuff structure has a bag-like structure expandable by fluid. This includes a tensile cuff, a pressing cuff, and a sensing cuff, for example. Also, the fluid includes a liquid and air. The bag-like structure is configured to be inflated by fluid, and is an air bag in a case where the fluid is air.

According to this aspect, the bag body that is stretchable is configured to have a length that allows the curler to be disposed and include the first hole portion into which the curler is inserted. Thus, the bag body, by elongating the bag body, allows the curler to be inserted from the first hole portion and thus the bag body can cover the outer circumferential surface of the curler when attached to the curler. Thus, the cover can prevent the curler and the cuff structure from becoming dirty, and because the cover is disposed between the wrist and the cuff structure, the wearability of the blood pressure measurement device can be improved.

Also, because the bag body has a stretchable configuration, the bag body stretches following to the expansion of the cuff structure, and thus the expansion of the cuff structure is not hindered. This allows the cover to cover the curler and the cuff without reducing the blood pressure measurement accuracy of the blood pressure measurement device. Also, by stretching the peripheral region of the first hole portion, the curler and the cuff structure can be disposed inside the bag body. This allows the cover to be easily attached to the curler and cuff structure.

In the cuff cover for the blood pressure measurement device according to the one aspect described above, the cuff cover for the blood pressure measurement device is provided in which the bag body includes a single cloth that is stacked at a portion facing the outer circumferential surface of the curler, and a weld sheet, for welding the cloth, provided at both ends in a longitudinal direction of the bag body and at the stacked portion of the cloth.

According to this aspect, a bag-like shape can be constituted by welding a single cloth, making manufacture simple. In addition, because the weld sheet is disposed at a portion facing the outer circumferential surface side of the curler in the bag-like shape, the cover has flexibility and stretchability at the portion facing the outer circumferential surface of the curler than at the portion facing the inner circumferential surface of the curler. Thus, the portion of the cover, provided with the weld sheet, on the outer circumferential surface side of the curler maintains its shape. And thus when the cover is attached to the curler, misalignment of the curler in the lateral direction can be prevented. In addition, the portion of the cover, formed only by the cloth, on the inner circumferential surface side of the curler is more flexible and stretchable than the portion on the outer circumferential surface side of the curler. This ensures that the expansion of the cuff structure is not hindered. Thus, the cover can be easily manufactured, does not reduce the blood pressure measurement accuracy of the blood pressure measurement device, and can prevent misalignment of the cover.

In the cuff cover for the blood pressure measurement device according to the one aspect described above, the cuff cover for the blood pressure measurement device is provided in which the first hole portion and the second hole portion are provided at the portion of the cloth to be stacked.

According to this aspect, in order to dispose the curler and the cuff structure in the bag body, the first hole portion into which the curler and the cuff structure are inserted is provided at the portion where the cloth is to be stacked and welded with the weld sheet. Thus, the portion where the first hole portion is provided is formed by two layers of the cloth and the weld sheet, and thus the strength can be improved while maintaining stretchability. Thus, even if the cover is repeatedly stretched when inserting the curler and the cuff structure, damage can be prevented, allowing the cover to be used repeatedly. Likewise, the second hole portion that exposes the power feeding terminal is provided at the portion of the cloth that is to be stacked and welded with the weld sheet. Thus, the portion where the second hole portion is provided is formed by two layers of the cloth and the weld sheet, and thus the strength can be improved while maintaining stretchability. Thus, even if an external force is repeatedly applied to the second hole portion by a connector or the like connected to the power feeding terminal, damage can be prevented.

In the cuff cover for the blood pressure measurement device according to the one aspect described above, the cuff cover for the blood pressure measurement device is provided in which the bag body has a width in a lateral direction that is formed to be greater than a width of the curler in a lateral direction.

According to this aspect, when the cover is attached to the curler and the cuff structure, play occurs in the cover, so it is possible to ensure a stretching margin of the bag body when the cuff structure is inflated. In this manner, pressing on the cuff structure in the direction facing the direction in which the cuff structure expands can be suppressed when the bag body is elongated. As a result, the cover can cover the curler and cuff structure without hindering the expansion of the cuff structure.

Advantageous Effects of Invention

According to the present invention, provided is a cuff cover for a blood pressure measurement device that can easily cover a curler and a cuff structure without reducing measurement accuracy.

BRIEF DESCRIPTION OF DRAWINGS

FIG. 1 is a perspective view illustrating a configuration of a blood pressure measurement device according to a first embodiment of the present invention.

FIG. 2 is a perspective view illustrating the configuration of the blood pressure measurement device.

FIG. 3 is an exploded perspective view illustrating the configuration of the blood pressure measurement device.

FIG. 4 is a side view illustrating the configuration of the blood pressure measurement device.

FIG. 5 is an explanatory diagram illustrating a state in which the blood pressure measurement device is attached to the wrist.

FIG. 6 is an explanatory diagram illustrating a state in which the blood pressure measurement device is attached to the wrist.

FIG. 7 is a block diagram illustrating the configuration of the blood pressure measurement device.

FIG. 8 is a perspective view illustrating the configuration of the blood pressure measurement device.

FIG. 9 is a perspective view illustrating the configuration of the blood pressure measurement device.

FIG. 10 is an exploded perspective view illustrating the configuration of a curler and a cuff structure of the blood pressure measurement device.

FIG. 11 is a cross-sectional view illustrating the configuration of the curler and the cuff structure of the blood pressure measurement device.

FIG. 12 is a cross-sectional view illustrating the configuration of the curler and the cuff structure of the blood pressure measurement device.

FIG. 13 is a cross-sectional view illustrating the configuration of a tensile cuff of the blood pressure measurement device.

FIG. 14 is a cross-sectional view illustrating the configuration of the tensile cuff of the blood pressure measurement device.

FIG. 15 is a perspective view illustrating the configuration of the curler of the blood pressure measurement device.

FIG. 16 is a plan view illustrating a configuration of the cuff structure of the blood pressure measurement device.

FIG. 17 is a plan view illustrating the configuration of the cuff structure.

FIG. 18 is a plan view illustrating a configuration of a pressing cuff of the blood pressure measurement device.

FIG. 19 is a cross-sectional view illustrating the configuration of the pressing cuff.

FIG. 20 is a plan view illustrating the configuration of a sensing cuff of the blood pressure measurement device.

FIG. 21 is a cross-sectional view illustrating the configuration of the sensing cuff.

FIG. 22 is a plan view illustrating the configuration of a cover of the blood pressure measurement device.

FIG. 23 is a plan view illustrating the configuration of a cloth and a weld sheet that form the cover.

FIG. 24 is a cross-sectional view illustrating the configuration of the cloth and the weld sheet.

FIG. 25 is a plan view illustrating an example of a method for manufacturing the cover.

FIG. 26 is a cross-sectional view illustrating an example of a method for manufacturing the cover.

FIG. 27 is a flowchart illustrating an example of a method for manufacturing the cover.

FIG. 28 is a flowchart illustrating an example of usage of the blood pressure measurement device.

FIG. 29 is a perspective view illustrating an example in which the blood pressure measurement device is attached to the wrist.

FIG. 30 is a perspective view illustrating an example in which the blood pressure measurement device is attached to the wrist.

FIG. 31 is a perspective view illustrating an example in which the blood pressure measurement device is attached to the wrist.

FIG. 32 is a cross-sectional view schematically illustrating a state in which the blood pressure measurement device is attached to the wrist.

DESCRIPTION OF EMBODIMENTS

First Embodiment

An example of cover 9 according to a first embodiment of the present invention and a blood pressure measurement device 1 using the cover 9 will be described below with reference to FIGS. 1 to 26.

FIG. 1 is a perspective view illustrating a configuration of the blood pressure measurement device 1 according to a first embodiment of the present invention. FIG. 2 is a perspective view illustrating the configuration of the blood pressure measurement device 1 and illustrating a state in which the cover 9 is detached. FIG. 3 is an exploded perspective view illustrating the configuration of the blood pressure measurement device 1. FIG. 4 is a side view illustrating the configuration of the blood pressure measurement device 1. FIG. 5 is an explanatory diagram illustrating a state in which the blood pressure measurement device 1 is attached to the wrist 200 and compressing the wrist 200. FIG. 6 is an explanatory diagram illustrating the blood pressure measurement device 1 attached to the wrist 200 and compressing the wrist 200 and illustrating a state in which the cover 9 is detached. FIG. 7 is a block diagram illustrating the configuration of the blood pressure measurement device 1. FIG. 8 is a perspective view illustrating the configuration of the blood pressure measurement device 1 with some configurations removed. FIG. 9 is a perspective view illustrating the configuration of the blood pressure measurement device 1 with some configurations removed and illustrating a state in which the cover 9 is detached. FIG. is an exploded perspective view illustrating the configuration of a curler 5 and a cuff structure 6 of the blood pressure measurement device 1. FIG. 11 is a cross-sectional view illustrating the configuration of the curler 5 and the cuff structure 6 of the blood pressure measurement device 1. FIG. 12 is a cross-sectional view illustrating the configuration of the curler 5 and the cuff structure 6 of the blood pressure measurement device 1.

FIG. 13 is a cross-sectional view illustrating the configuration of a tensile cuff 74 of the blood pressure measurement device 1. FIG. 14 is a cross-sectional view illustrating the configuration of the tensile cuff 74 of the blood pressure measurement device 1. FIG. 15 is a perspective view illustrating the configuration of the curler 5 of the blood pressure measurement device 1. FIG. 16 is a plan view illustrating a configuration of the cuff structure 6 of the blood pressure measurement device 1 from the wrist 200 side. FIG. 17 is a plan view illustrating the configuration of the curler 5 of the cuff structure 6 on the inner circumferential surface side.

FIG. 18 is a plan view illustrating the configuration of a pressing cuff 71 of the blood pressure measurement device 1. FIG. 19 is a cross-sectional view illustrating the configuration of the pressing cuff 71, which is a line cross-section along XIX-XIX illustrated in FIG. 18. FIG. 20 is a plan view illustrating the configuration of a sensing cuff 73 of the blood pressure measurement device 1. FIG. 21 is a cross-sectional view illustrating the configuration of the sensing cuff 73 of the blood pressure measurement device 1, which is a line cross-section along XXI-XXI illustrated in FIG. 20. FIG. 22 is a plan view illustrating the configuration of a cover 9 of the blood pressure measurement device 1. FIG. 23 is a plan view illustrating the configuration of a cloth 131 and a weld sheet 132 that form the cover 9. FIG. 24 is a cross-sectional view illustrating the configuration of the cloth 131 and the weld sheet 132, which is a line cross-section along XXIV-XXIV illustrated in FIG. 23. FIG. 25 is a plan view illustrating the cloth 131 and the weld sheet 132 in a folded state, as an example of a method for manufacturing the cover 9. FIG. 26 is a cross-sectional view illustrating the cloth 131 and the weld sheet 132 in a folded state, as an example of a method for manufacturing the cover 9, which is a line cross-section along XXVI-XXVI illustrated in FIG. 25.

The blood pressure measurement device 1 is an electronic blood pressure measurement device attached to a living body. The present embodiment will be described using an electronic blood pressure measurement device having an aspect of a wearable device attached to the wrist 200 of the living body.

As illustrated in FIGS. 1 to 7, the blood pressure measurement device 1 includes a device body 3, a belt 4 that fixes the device body 3 at the wrist, the curler 5 disposed between the belt 4 and the wrist, the cuff structure 6 including the pressing cuff 71, the sensing cuff 73, and the tensile cuff 74, a fluid circuit 7 fluidly connecting the device body 3 and the cuff structure 6, and power feeding unit 8 provided on the curler 5, and the cover (cuff cover for a blood pressure measurement device) 9 that covers the curler 5 and the cuff structure 6.

As illustrated in FIGS. 1 to 7, the device body 3 includes, for example, a case 11, a display unit 12, an operation unit 13, a pump 14, the flow path portion 15, the on-off valve 16, the pressure sensor 17, a power supply unit 18, a vibration motor 19, and a control substrate 20. The device body 3 supplies a fluid to the cuff structure 6 using the pump 14, the on-off valve 16, the pressure sensor 17, the control substrate 20, and the like.

As illustrated in FIGS. 1 to 3, the case 11 includes an outer case 31, a windshield 32 covering an opening of the outer case 31 on the opposite side (outer side) to the wrist 200 side, a base portion 33 provided inside the outer case 31 on the wrist 200 side, a rear cover 35 covering the wrist 200 side of the outer case 31, and a sealing member 36 provided on the lower surface of the rear cover 35.

The outer case 31 is formed in a cylindrical shape. The outer case 31 includes pairs of lugs 31a provided at respective symmetrical positions in the circumferential direction of an outer circumferential surface, and spring rods 31b each provided between each of the two pairs of lugs 31a. The windshield 32 is, for example, a circular glass plate.

The base portion 33 holds the display unit 12, the operation unit 13, the pump 14, the on-off valve 16, the pressure sensor 17, the power supply unit 18, the vibration motor 19, and the control substrate 20. Additionally, the base portion 33 constitutes a portion of the flow path portion 15 that makes the pump 14 and the cuff structure 6 fluidly continuous.

The rear cover 35 is configured as an annular shape with an open center. The rear cover 35 covers the end portion on the outer peripheral edge side of the outer case 31 on the wrist 200 side. With the rear cover 35 configured as such being integrally assembled with the curler 5, the central opening is covered by the curler 5, and the rear cover 35 together with the curler 5 forms a rear lid covering the end portion of the outer case 31 on the wrist 200 side. Specifically, the rear cover 35 is fixed to the curler 5 with four first joining members 35a and fixed to the end portion of the outer case 31 on the wrist 200 side with four second joining members 35b. The rear cover 35 includes four hole portions 35c into which the first joining members 35a that are provided at the bottom portion and fixed to the curler 5 are inserted, and four hole portions 35d provided at four portions of the outer circumferential portion that radially project out, into which the second joining members 35b that are fixed to the outer case 31 are inserted.

The first joining members 35a and the second joining members 35b are members, such as a screw, a bolt, a machine screw, a rive, for mechanically joining two components. In the present embodiment, the first joining members 35a and the second joining members 35b are screws.

The sealing member 36 is a double-sided tape, for example, formed in the shape of the region of the rear cover 35 that comes into contact with the curler 5. The sealing member 36 seals between the curler 5 and the rear cover 35 by being provided between the curler 5 and the rear cover 35.

The display unit 12 is disposed on the base portion 33 of the outer case 31 and directly below the windshield 32. As illustrated in FIG. 7, the display unit 12 is electrically connected to the control substrate 20. The display unit 12 is, for example, a liquid crystal display or an organic electroluminescence display. The display unit 12 displays various types of information including the date and time and measurement results of blood pressure values such as the systolic blood pressure and diastolic blood pressure, heart rate, and the like.

The operation unit 13 is configured to be capable of receiving an instruction input from a user. For example, the operation unit 13 includes a plurality of buttons 41 provided on the case 11, a sensor 42 that detects operation of the buttons 41, and a touch panel 43 provided on the display unit 12 or the windshield 32, as illustrated in FIGS. 1 and 7. When operated by the user, the operation unit 13 converts an instruction into an electrical signal. The sensor 42 and the touch panel 43 are electrically connected to the control substrate 20 to output electrical signals to the control substrate 20.

As the plurality of buttons 41, for example, three buttons are provided. The buttons 41 are supported by the base portion 33 and protrude from the outer circumferential surface of the outer case 31. The plurality of buttons 41 and a plurality of the sensors 42 are supported by the base portion 33. The touch panel 43 is integrally provided on the windshield 32, for example.

The pump 14 is, for example, a piezoelectric pump. The pump 14 compresses air and supplies compressed air to the cuff structure 6 through the flow path portion 15. The pump 14 is electrically connected to the control substrate 20.

The flow path portion 15 constitutes the flow path connecting from the pump 14 to the pressing cuff 71 and the tensile cuff 74 and a flow path connecting from the pump 14 to the sensing cuff 73, as illustrated in FIG. 7. Additionally, the flow path portion 15 constitutes a flow path connecting from the pressing cuff 71 and the tensile cuff 74 to the atmosphere, and a flow path connecting from the sensing cuff 73 to the atmosphere. The flow path portion 15 is a flow path of air constituted by a hollow portion, a groove, a flow path tank, a tube, or the like provided in the base portion 33 and the like.

The on-off valve 16 opens and closes a portion of the flow path portion 15. Specifically, a plurality of on-off valves 16, specifically four on-off valves 16 are provided, for example, as illustrated in FIG. 7, and selectively open and close the flow path connecting from the pump 14 to the pressing cuff 71 and the tensile cuff 74, the flow path connecting from the pump 14 to the sensing cuff 73, the flow path connecting from the pressing cuff 71 and the tensile cuff 74 to the atmosphere, and the flow path connecting from the sensing cuff 73 to the atmosphere, by the combination of opening and closing of each of the on-off valves 16. As a specific example, the four on-off valves 16 are constituted by the first on-off valve 16A, the second on-off valve 16B, the third on-off valve 16C, and the fourth on-off valve 16D. The first on-off valve 16A opens and closes the flow path connecting the pump 14 and the sensing cuff 73. The second on-off valve 16B opens and closes the flow path connecting the pump 14 and the tensile cuff 74. The second on-off valve 16B and the third on-off valve 16C open and close the flow path connecting the pump 14 and the pressing cuff 71. The second on-off valve 16B, the third on-off valve 16C, and the fourth on-off valve 16D open and close the flow path connecting the pump 14 and the atmosphere.

The pressure sensor 17 at least detects the pressure of the sensing cuff 73. The pressure sensor 17 is provided with the first pressure sensor 17A and the second pressure sensor 17B, for example. The pressure sensor 17 converts a detected pressure into an electrical signal, and outputs the electrical signal to the control substrate 20. For example, the first pressure sensor 17A and the second pressure sensor 17B are provided in the flow path connecting the first on-off valve 16A of the flow path portion and the sensing cuff 73. The flow path is continuous through the pressing cuff 71, the sensing cuff 73, and the tensile cuff 74 to the pump 14 by the opening and closing of each of the on-off valves, and thus the pressure in these flow paths corresponds to the pressure in the internal space of the pressing cuff 71, the sensing cuff 73, and the tensile cuff 74 connecting to the pump 14.

Specifically, for example, the pressure sensor 17 detects the pressure of the sensing cuff 73, i.e., the pressure of the flow path portion 15 connecting the pump 14 and the sensing cuff 73, when the first on-off valve 16A is open and the second on-off valve 16B is closed. Also, the pressure sensor 17 detects the pressure of the sensing cuff 73 and the tensile cuff 74, i.e., the pressure of the flow path portion 15 connecting the pump 14, the sensing cuff 73, and the tensile cuff 74, when the first on-off valve 16A and the second on-off valve 16B are open and the third on-off valve 16C is closed. Furthermore, the pressure sensor 17 detects the pressure of the pressing cuff 71, the sensing cuff 73, and the tensile cuff 74, i.e., the pressure of the flow path portion 15 connecting the pump 14, the pressing cuff 71, the sensing cuff 73, and the tensile cuff 74, when the first on-off valve 16A, the second on-off valve 16B, and the third on-off valve 16C are open and the fourth on-off valve 16D is open or closed.

The power supply unit 18 is, for example, a secondary battery such as a lithium ion battery. The power supply unit 18 is electrically connected to the control substrate 20, as illustrated in FIG. 7. The power supply unit 18 supplies power to the control substrate 20.

As illustrated in FIG. 7, the control substrate 20 includes, for example, a substrate 51, an acceleration sensor 52, a communication unit 53, a storage unit 54, and a control unit 55. The control substrate 20 is constituted by the acceleration sensor 52, the communication unit 53, the storage unit 54, and the control unit 55 that are mounted on the substrate 51.

The substrate 51 is fixed to the base portion 33 of the case 11 using screws or the like.

The acceleration sensor 52 is, for example, a 3-axis acceleration sensor. The acceleration sensor 52 outputs, to the control unit 55, an acceleration signal representing acceleration of the device body 3 in three directions orthogonal to one another. For example, the acceleration sensor 52 is used to measure, from the detected acceleration, the amount of activity of a living body to which the blood pressure measurement device 1 is attached.

The communication unit 53 is configured to be capable to transmit and receive information to and from an external device wirelessly or by wire. For example, the communication unit 53 transmits information controlled by the control unit 55, and information of a measured blood pressure value, a pulse, and the like to an external device via a network, and receives a program or the like for software update from an external device via a network and sends the program or the like to the control unit 55.

In the present embodiment, the network is, for example, the Internet, but is not limited to this. The network may be a network such as a Local Area Network (LAN) provided in a hospital or may be direct communication with an external device using a cable or the like including a terminal of a predetermined standard such as a USB. Thus, the communication unit 53 may be configured to include a plurality of wireless antennas, micro-USB connectors, or the like.

The storage unit 54 pre-stores program data for controlling the overall blood pressure measurement device 1 and a fluid circuit 7, settings data for setting various functions of the blood pressure measurement device 1, calculation data for calculating a blood pressure value and a pulse from pressure measured by the pressure sensors 17, and the like. Additionally, the storage unit 54 stores information such as a measured blood pressure value and a measured pulse.

The control unit 55 is constituted by one or more CPUs, and controls operation of the overall blood pressure measurement device 1 and operation of the fluid circuit. The control unit 55 is electrically connected to and supplies power to the display unit 12, the operation unit 13, the pump 14, each of the on-off valves 16 and the pressure sensors 17. Additionally, the control unit 55 controls operation of the display unit 12, the pump 14, and the on-off valves 16, based on electrical signals output by the operation unit 13 and the pressure sensors 17.

For example, as illustrated in FIG. 7, the control unit 55 includes a main Central Processing Unit (CPU) 56 that controls operation of the overall blood pressure measurement device 1, and a sub-CPU 57 that controls operation of the fluid circuit 7. For example, the main CPU 56 obtains measurement results such as blood pressure values, for example, the systolic blood pressure and the diastolic blood pressure, and the heart rate, from electrical signals output by the pressure sensor 17, and outputs an image signal corresponding to the measurement results to the display unit 12.

For example, the sub-CPU 57 drives the pump 14 and the on-off valves 16 to feed compressed air to the pressing cuff 71 and the sensing cuff 73 when an instruction to measure the blood pressure is input from the operation unit 13. In addition, the sub-CPU 57 controls driving and stopping of the pump 14 and opening and closing of the on-off valves 16 based on electrical signal output by the pressure sensors 17. The sub-CPU 57 controls the pump 14 and the on-off valves 16 to selectively feed compressed air to the pressing cuff 71 and the sensing cuff 73 and selectively depressurize the pressing cuff 71 and the sensing cuff 73.

As illustrated in FIGS. 1 to 6, the belt 4 includes a first belt 61 provided on the first pair of lugs 31a and the spring rod 31b, and a second belt 62 provided on the second pair of lugs 31a and the spring rod 31b. The belt 4 is wrapped around the wrist 200 with a curler 5 in between.

The first belt 61 is referred to as a so-called a parent and is configured like a band capable of being joined to the second belt 62. As illustrated in FIGS. 1 to 3, the first belt 61 includes a belt portion 61a and a buckle 61b. The belt portion 61a is configured like a band. The belt portion 61a is formed of an elastically deformable resin material. In addition, the belt portion 61a is flexible and includes a sheet-like insert member inside the belt portion 61a for suppressing stretching in the longitudinal direction of the belt portion 61a. The belt portion 61a includes a first hole portion 61c that is formed at one end portion and extends orthogonal to the longitudinal direction of the belt portion 61a, and a second hole portion 61d that is formed at the other end portion and extends orthogonal to the longitudinal direction of the first belt 61.

As illustrated in FIGS. 5, 6, and 8, the first hole portion 61c is provided at the end portion of the belt portion 61a. The first hole portion 61c has an inner diameter at which the spring rod 31b can be inserted into the first hole portion 61c and at which the first belt 61 can rotate with respect to the spring rod 31b. In other words, the first belt 61 is rotatably held by the outer case 31 by disposing the first hole portion 61c between the pair of lugs 31a and around the spring rod 31b.

As illustrated in FIGS. 1 and 3, the second hole portion 61d is provided at the leading end of the belt portion 61a. The buckle 61b is attached to the second hole portion 61d.

As illustrated in FIGS. 1 and 3, the buckle 61b includes a frame body 61e in a rectangular frame shape and a prong 61f rotatably attached to the frame body 61e. A side of the frame body 61e to which the prong 61f is attached is inserted into the second hole portion 61d, and the frame body 61e is mounted rotatably with respect to the belt portion 61a.

The second belt 62 is referred to as a so-called blade tip, and is configured in a band-like shape having a width at which the second belt 62 can be inserted into the frame body 61e. The second belt 62 is formed of an elastically deformable resin material. In addition, the second belt 62 is flexible and includes a sheet-like insert member inside the second belt 62 for suppressing stretching in the longitudinal direction of the second belt 62.

In addition, as illustrated in FIGS. 1 and 2, the second belt 62 includes a plurality of small holes 62a into which the prong 61f is inserted. Additionally, the second belt 62 includes a third hole portion 62b provided at first end portion of the second belt 62 and extending orthogonally to the longitudinal direction of the second belt 62. The third hole portion 62b has an inner diameter at which the spring rod 31b can be inserted into the third hole portion 62b and at which the second belt 62 can rotate with respect to the spring rod 31b. In other words, the second belt 62 is rotatably held by the outer case 31 by disposing the third hole portion 62b between the pair of lugs 31a and around the spring rod 31b.

The second belt 62 is inserted into the frame body 61e, and the prong 61f is inserted into the small hole 62a, and thus the first belt 61 and the second belt 62 are integrally connected together, and the belt 4 as described above, together with the outer case 31, comes to have an annular shape following along the circumferential direction of the wrist 200. By shaping the belt 4 in an annular shape following along the circumferential direction of the wrist 200, the curler 5 is pressed and elastically deformed to follow along the circumferential direction of the wrist of the wearer of the blood pressure measurement device 1.

As illustrated in FIGS. 1 to 3 and 6, the curler 5 is configured in a band-like shape that curves in such a manner as to follow along the circumferential direction of the wrist 200. The curler 5 is formed with a first end and a second end spaced apart from each other. For example, a first end side outer surface of the curler 5 is fixed to the rear cover 35 of the device body 3. The curler 5 is disposed at a position where the first end and the second end protrude more to one side of the wrist 200 than the rear cover 35. Accordingly, the curler 5 is disposed with the first end and the second end to one side of the wrist 200 when the blood pressure measurement device 1 is attached to the wrist 200. Furthermore, the first end and the second end of the curler 5 are located adjacent to each other at a predetermined distance from each other. The curler is formed of a resin material, for example. In a specific example, the curler 5 is formed of a polypropylene with a thickness of approximately 1 mm.

In a specific example, as illustrated in FIGS. 1 to 3 and 6, the curler 5 is configured in a band-like shape that curves following along the circumferential direction of the wrist. Furthermore, the curler 5 includes the disk-like cover portion 5a provided at a position facing the backhand side of the wrist 200 on the first end side, and constitutes the rear lid together with the rear cover 35, and an escape portion 5b that is provided in the peripheral region of the cover portion 5a and allows the second joining members 35b that fix the outer case 31 and the rear cover 35 to be moveable. For example, the cover portion 5a and the adjacent portion of the cover portion 5a of the curler 5 are formed in a plate-like shape, and the first and second end sides is formed curving with a predetermined curvature more than the cover portion 5a. Furthermore, the length of the curler 5 from the cover portion 5a to the first end is less than the length from the cover portion 5a to the second end. In a specific example, the shorter side of the curler 5 from the cover portion 5a to the first end is disposed on the backhand side of the wrist, and the longer side from the cover portion 5a to the second end extends from the backhand side of the wrist, passing through one side, to the hand palm-side of the wrist 200.

Additionally, as illustrated in FIG. 15, the curler 5 is formed in a shape with the second end located at the inner circumferential surface side of the first end side when the first end and the second end are brought close. In a specific example, the width of the curler 5 in the width direction of the wrist 200 is set to be greater on the backhand side of the wrist 200 than on the hand palm-side of the wrist 200. Furthermore, the radius of curvature of the first end of the curler 5 on the backhand side of the wrist 200 is set to be greater than the radius of curvature of the second end on the hand palm-side of the wrist 200. According to such a configuration, when both end sides of the curler 5 are brought to abut, the second end is disposed further to the inward side of the curler 5 than the first end. Furthermore, the curler 5 is provided with a recess 5c provided adjacent to the cover portion 5a on a portion of the cover portion 5a, on the outer surface on the first end side from the cover portion 5a, and also on the outer surface on the shorter side extending from the cover portion 5a.

The cover portion 5a includes an insert member 5d for reinforcement which is inserted. The cover portion 5a is fixed to the wrist 200 side of the outer case 31 with the fixed rear cover 35 in between. The cover portion 5a includes screw holes 5e provided at positions facing the four hole portions 35c of the rear cover 35, into which the first joining members 35a for fixing the rear cover 35 are screwed, and includes three hole portions 5f for connecting the cuff structure 6 to the device body 3.

The escape portion 5b is a relief for disposing the second joining members 35b in the rear cover 35 and for disposing a tool for rotating the second joining members 35b in a manner so that the second joining members 35b do not interfere with the curler when the rear cover 35 is fixed to the outer case 31 from the rear cover 35 side with the second joining members 35b.

The three hole portions 5f include a first hole portion 5f1 formed with an inner diameter into which a connection portion 84 described below of the pressing cuff 71 can be inserted, a second hole portion 5f2 formed with an inner diameter into which a connection portion 93 described below of the sensing cuff 73 can be inserted, and the third hole portion 5f3 formed with an inner diameter into which a connection portion 103 described below of the tensile cuff 74 can be inserted. In the present embodiment, the second hole portion 5f2 is disposed in the cover portion 5a closer to the second end side on the hand palm-side of the curler 5 than the first hole portion 5f1 and the third hole portion 5f3.

The curler 5 with such a configuration is fixed to the outer case 31 with the first end and the second end orientated to face the second belt 62 of the belt 4. Also, the curler 5 at least at the position facing the hand palm-side of the wrist 200 curves along the circumferential direction along with the hand palm-side of the wrist 200, and thus the cuff structure 6 facing the hand palm-side of the wrist 200 is held in a curved state following along the shape of the hand palm-side of the wrist 200.

The curler 5 has a hardness appropriate to provide flexibility and shape retainability. Here, "flexibility" refers to deformation of the shape of the curler 5 in a radial direction at the time of application of an external force of the belt 4 to the curler 5. For example, "flexibility" refers to deformation of the shape of the curler 5 in a side view in which the curler 5 approaches the wrist, is along the shape of the wrist, or follows to the shape of the wrist when the curler 5 is pressed by the belt 4. Furthermore, "shape retainability" refers to the ability of the curler 5 to maintain a pre-imparted shape when no external force is applied to the curler 5. For example, "shape retainability" refers to, in the present embodiment, the ability of the curler 5 to maintain the shape in a shape curving along the circumferential direction of the wrist.

The cuff structure 6 is disposed on an inner circumferential surface of the curler 5, and is held along the shape of the inner circumferential surface of the curler 5. As a specific example, the cuff structure 6 is held by disposing the pressing cuff 71 and the tensile cuff 74 on the inner circumferential surface of the curler 5, and fixing the cuff structure 6 by a joining layer 75 provided between the curler 5 and the pressing cuff 71 and the tensile cuff 74. In the present embodiment, the joining layer 75 is adhesive or double-sided tape.

As illustrated in FIGS. 2, 3, 16, and 17, the cuff structure 6 includes the pressing cuff 71, a back plate 72, the sensing cuff 73, and the tensile cuff 74. Also, the cuff structure 6 is provided with the joining layer 75 for joining components each other and joining the curler 5 and the cuffs 71 and 74. The cuff structure 6 is fixed to the curler 5. The cuff structure 6 includes the pressing cuff 71, the back plate 72, and the sensing cuff 73 that are stacked one another and disposed on the curler 5, and the tensile cuff 74 that is spaced apart from the pressing cuff 71, the back plate 72, and the sensing cuff 73 and disposed on the curler 5.

In a specific example, as illustrated in FIG. 6, the cuff structure 6 is fixed to the inner circumferential surface of the curler 5 on the hand palm-side of the wrist 200 with the pressing cuff 71, the back plate 72, and the sensing cuff 73 stacked in this order from the inner circumferential surface of the curler 5 toward the wrist 200 side. In addition, the cuff structure 6 includes the tensile cuff 74 disposed on the inner circumferential surface of the curler 5 on the backhand side of the wrist 200. Each of the members of the cuff structure 6 is fixed to an adjacent member of the cuff structure 6 in a stacking direction by the joining layer 75.

The pressing cuff 71 is fluidly connected to the pump 14 through the flow path portion 15. The pressing cuff 71 is inflated to pressing the back plate 72 and the sensing cuff 73 toward the wrist 200 side. As illustrated in FIGS. 11, 12, and 16 to 19, the pressing cuff 71 includes a plurality of, for example, two-layer air bags 81, a target join portion 82 provided on the air bag 81 facing the curler 5, a flow path body 83 communicating with the air bags 81, and the connection portion 84 provided in the leading end of the flow path body 83. The pressing cuff 71 with such a configuration is configured by integrally welding a plurality of sheet members 86 together.

Here, the air bags 81 are bag-like structures, and in the present embodiment, the blood pressure measurement device 1 is configured to use air with the pump 14, and thus the present embodiment will be described using the air bags. However, in a case where a fluid other than air is used, the bag-like structures may be fluid bags that is inflated by a fluid. The plurality of air bags 81 are stacked and are in fluid communication with one another in the stacking direction.

Each of the air bags 81 is formed in a rectangular bag-like shape that is long in one direction. Additionally, the air bags 81 are set so that the width in the lateral direction is the same as the width in the lateral direction of the curler 5. The air bags 81 are each constituted by, for example, combining two sheet members 86 and, as illustrated in FIGS. 11, 12, and 16 to 19, welding a weld portion 81a using heat into a rectangular frame shape long in one direction. In addition, the two-layer air bags 81 are constituted by forming with integrally combining two air bags 81 by welding using heat, or with welding together a pair of sheet members 86 facing adjacent air bag 81 and welding to the air bag 81. In a specific example, the two-layer air bags 81 are fluidly continuous through openings provided in the sheet members 86 facing one another. In addition, in the two-layer air bags 81, by bridge welding the opposing sheet members 86 together with a quadrilateral frame shape smaller than the weld portion 81a located on the outer peripheral edge and surrounding the plurality of openings with this bridge weld portion (join portion) 81b, the adjacent air bags 81 are integrally formed and make fluidly continuous on the inner side of the bridge weld portion 81b.

A single or a plurality of target join portions 82 are provided at at least a portion of the edge portion of the air bag 81 disposed adjacent to the curler 5. The target join portion 82 is formed by a portion of the sheet member 86 forming the air bag 81.

An example of the present embodiment will be described using the examples illustrated in FIGS. 11, 12, and 16 to 19 in which one target join portion 82 is provided on the edge portion in the lateral direction of each of the air bags 81. Note that, for example, the target join portion 82 may be divided in the longitudinal direction of the air bag 81 by a slit, or a plurality of target join portions 82 may be provided in the longitudinal direction of the air bag 81. The target join portion 82 is at least joined to the outer circumferential surface of the curler 5 when the pressing cuff 71 is disposed on the inner circumferential surface of the curler 5. Furthermore, for example, two target join portions 82 are stacked and welded.

Note that the two target join portions 82 are set to have a different length to the length in the lateral direction of the air bags 81, for example. In this example, the two target join portions 82 are stacked and welded at the first end side in the lateral direction of the curler 5. Note that as long as the two target join portions 82 are able to be disposed with the leading end on the outer circumferential surface of the curler 5, the length is able to be set as appropriate, and the two target join portions 82 may be stackable or not. However, in a case where the length is set to a stackable length, the length is preferably a length such that the leading end does not extend further out than the outer edge of the outer circumferential surface of the curler 5.

As illustrated in FIGS. 10 and 16 to 19, the flow path body 83 is integrally provided on a single air bag 81, for example, on a portion of one edge portion in the longitudinal direction of the air bag 81 adjacent to the curler 5. As a specific example, the flow path body 83 is provided at the end portion of the air bag 81 near the device body 3. Additionally, the flow path body 83 is formed in a shape that is long in one direction and has less width than the width of the air bag 81 in the lateral direction and formed with a leading end having a circular shape. The flow path body 83 includes the connection portion 84 on the leading end. The flow path body 83 is connected to the flow path portion 15 through the connection portion 84 and constitutes a flow path between the flow path portion 15 of the device body 3 and the air bag 81.

The flow path body 83 is constituted by welding a portion of sheet members 86, which is adjacent to a region of the sheet members 86 constituting the air bags 81, in a frame shape long in one direction using heat, in a state where the connection portion 84 is disposed on the two sheet members 86. The flow path body 83 with such a configuration is disposed between the inner circumferential surface of the curler 5 and the tensile cuff 74, and the leading end is disposed at a position facing the first hole portion 5/1 on the main surface on the wrist 200 side of the region where the cover portion 5a of the curler 5 is provided. In addition, the width of the flow path body 83 not including a weld portion 83a is formed to be 3.8 mm, for example.

Note that, a portion of the weld portion 81a, where the two sheet members 86 are welded in a rectangular frame shape, is not welded and the air bags 81 provided with the flow path body 83 are constituted to be continuous with the weld portion 83a constituting the flow path body 83, and thus the air bags 81 are fluidly continuous with the flow path body 83.

The connection portion 84 is, for example, a nipple. The connection portion 84 is provided at the leading end of the flow path body 83. The leading end of the connection portion 84 is exposed from the sheet member 86, facing the curler 5, of the two sheet members 86 constituting the flow path body 83. The connection portion 84 is inserted in the first hole portion 5f1 of the cover portion 5a and is connected to the flow path portion 15.

As a specific example, as illustrated in FIGS. 11, 12, and 32, the pressing cuff 71 includes a first sheet member 86a, a second sheet member 86b, a third sheet member 86c, and a fourth sheet member 86d in this order from the wrist 200 side. The second sheet member 86b constitutes a first-layer air bag 81 along with the first sheet member 86a, the third sheet member 86c is integrally joined to the second sheet member 86b and constitutes the target join portion 82, and the fourth sheet member 86d constitutes a second-layer air bag 81 and the flow path body 83 along with the third sheet member 86c. Note that the pressing cuff 71 is integrally constituted by joining adjacent sheet members 86 by welding using heat.

The first sheet member 86a and the second sheet member 86b are configured in a similar rectangular shape to the air bags 81, and peripheral edge portions of the four sides are welded to constitute the air bags 81. The second sheet member 86b and the third sheet member 86c are disposed facing each other, and each includes a plurality of openings 86b1 and 86c1 through which the two air bags 81 are fluidly continuous. Additionally, the second sheet member 86b and the third sheet member 86c are integrally joined by the peripheral region of the plurality of openings 86b1 and 86c1 being welded using heat in a quadrilateral frame shape smaller than the welded four sides of the air bags 81.

The third sheet member 86c, for example, is constituted in a shape that allows the air bags 81, the target join portion 82, and the flow path body 83 to be constituted. The fourth sheet member 86d, for example, is constituted in a shape that allows the air bags 81 and the flow path body 83 to be constituted. Furthermore, the fourth sheet member 86d includes a hole portion 86d1 into which the leading end of the connection portion 84 can be inserted, for example.

The air bags 81, the target join portion 82, and the flow path body 83 are constituted by the third sheet member 86c and the fourth sheet member 86d being disposed facing one another, welded using heat along the peripheral edge shape of the air bag 81 and the flow path body 83 so that the air bag 81 and the flow path body 83 are fluidly continuous, and cut in a predetermined shape.

The hole portion 86d1 of the fourth sheet member 86d is disposed with the connection portion 84, and the peripheral region of the hole portion 86d1 is welded to the connection portion 84 using heat. Furthermore, the fourth sheet member 86d is joined with the inner circumferential surface of the curler 5 with the joining layer 75 in between, and the target join portion 82 of the third sheet member 86c is joined to the outer circumferential surface of the curler 5 with the joining layer 75 in between.

As illustrated in FIGS. 11, 12, and 32, the back plate 72 is applied to the outer surface of the first sheet member 86a of the pressing cuff 71 by the joining layer 75. The back plate 72 is formed in a plate shape using a resin material. The back plate 72 is made of polypropylene, for example, and is formed into a plate shape having a thickness of approximately 1 mm. The back plate 72 has shape followability.

Here, "shape followability" refers to a function of the backplate 72 by which the back plate 72 can be deformed in such a manner as to follow the shape of a contacted portion of the wrist 200 to be disposed, the contacted portion of the wrist 200 refers to a region of the wrist 200 that is faced by the back plate 72. Here, the contact as used herein includes both direct contact and indirect contact with the sensing cuff 73 in between.

For example, as illustrated in FIG. 12, the back plate 72 includes a plurality of grooves 72a extending in both main surfaces in a direction orthogonal to the longitudinal direction. The plurality of grooves 72a face the corresponding grooves 72a provided in the other main surface in the thickness direction of the back plate 72. Additionally, the plurality of grooves 72a are disposed at equal intervals in the longitudinal direction of the back plate 72.

In the back plate 72, portions including the plurality of grooves 72a are thinner than portions including no grooves 72a and thus the portions including the plurality of grooves 72a are easily deformed. Accordingly, the back plate 72 is deformed in such a manner as to follow to the shape of the wrist 200, and has shape followability of extending in the circumferential direction of the wrist. The back plate 72 is formed such that the length of the back plate 72 is sufficient to cover the hand palm-side of the wrist 200. The back plate 72 transfers the pressing force from the pressing cuff 71 to the back plate 72 side main surface of the sensing cuff 73 in a state in which the back plate 72 is extending along the shape of the wrist 200.

The sensing cuff 73 is fluidly connected to the pump 14 through the flow path portion 15. The sensing cuff 73 is fixed to the main surface of the back plate 72 on the wrist 200 side. The sensing cuff 73 is in direct contact with a region of the wrist 200 where an artery 210 resides, as illustrated in FIGS. 6 and 32. The artery 210 as used herein is the radial artery and the ulnar artery. The sensing cuff 73 is formed in the same shape as that of the back plate 72 or a shape that is smaller than that of the back plate 72, in the longitudinal direction and the width direction of the back plate 72. The sensing cuff 73 is inflated to compress a hand palm-side region of the wrist 200 in which the artery 210 resides. The sensing cuff 73 is pressed by the inflated pressing cuff 71 toward the wrist 200 side with the back plate 72 in between.

In a specific example, as illustrated in FIGS. 11, 12, 16, 17, 20, and 21, the sensing cuff 73 includes one air bag 91, a flow path body 92 that communicates with the air bag 91, and the connection portion 93 provided at the leading end of the flow path body 92. One main surface of the air bag 91 of the sensing cuff 73 is fixed to the back plate 72. For example, the sensing cuff 73 is joined to the main surface of the back plate 72 on the wrist 200 side by the joining layer 75. The sensing cuff 73 with such a configuration is constituted by welding two sheet members 96.

Here, the air bag 91 is a bag-like structure, and in the present embodiment, the blood pressure measurement device 1 is configured to use air with the pump 14, and thus the present embodiment will be described using the air bag. However, in a case where a fluid other than air is used, the bag-like structure may be a fluid bag and the like.

The air bag 91 is constituted in a rectangular shape that is long in one direction. The air bags 91 are each constituted by, for example, combining two sheet members 96 long in one direction and, as illustrated in FIGS. 11, 12, 16, 17, 20, and 21, welding a weld portion 91a using heat into a rectangular frame shape long in one direction. Also, the air bag 91, for example, includes a junction margin 91b for ensuring area for joining the air bag 91 to the back plate 72 using the joining layer 75. The junction margin 91b is formed by the sheet member 96 facing the back plate 72, for example.

The flow path body 92 is integrally provided at a portion of one edge portion of the air bag 91 in the longitudinal direction. As a specific example, the flow path body 92 is provided at the end portion of the air bag 91 near the device body 3. Additionally, the flow path body 92 is formed in a shape that is long in one direction and has less width than the width of the air bag 91 in the lateral direction, and formed with a leading end having a circular shape. The flow path body 92 includes the connection portion 93 on the leading end. The flow path body 92 is connected to the flow path portion 15 through the connection portion 93 and constitutes a flow path between the flow path portion 15 of the device body 3 and the air bag 91.

The flow path body 92 is constituted by welding a portion of sheet members 96, which is adjacent to a region of the sheet members 96 constituting the air bag 91, in a frame shape long in one direction using heat, in a state where the connection portion 93 is disposed on the two sheet members 96. Note that, a portion of the weld portion 91a, where the two sheet members 96 are welded in a rectangular frame shape, is not welded and the air bag 91 is constituted to be continuous with the weld portion 92a constituting the flow path body 92, and thus the air bag 91 and the flow path body 92 are fluidly continuous. The flow path body 92 with such a configuration is disposed between the inner circumferential surface of the curler 5 and the tensile cuff 74, and the leading end is disposed at a position facing the second hole portion 5f2 on the main surface on the wrist 200 side of the region where the cover portion 5a of the curler 5 is provided. In addition, the width of the flow path body 92 not including the weld portion 92a is 3.8 mm, for example.

The connection portion 93 is, for example, a nipple. The connection portion 93 is provided at the leading end of the flow path body 92. Also, the leading end of the connection portion 93 is externally exposed from the sheet member 96 facing the curler 5 and the back plate 72, of the two sheet members 96 constituting the flow path body 92. The connection portion 93 is inserted in the second hole portion 5f2 of the cover portion 5a and is connected to the flow path portion 15.

In a specific example, the sensing cuff 73 includes a fifth sheet member 96a and a sixth sheet member 96b in this order from the wrist 200 side as illustrated in FIGS. 11 and 12. Note that the sensing cuff 73 is constituted by joining adjacent sheet members 96 by welding using heat.

For example, the fifth sheet member 96a and the sixth sheet member 96b are constituted in a shape that allows the air bag 91, the junction margin 91b, and the flow path body 92 to be constituted. The air bag 91 and the flow path body 92 are constituted by the fifth sheet member 96a and the sixth sheet member 96b being disposed facing one another, welded using heat along the peripheral edge shape of the air bag 91 and the flow path body 92 so that the air bag 91 and the flow path body 92 are fluidly continuous, and cut in a predetermined shape.

Furthermore, the sixth sheet member 96b includes a hole portion 96b1 into which the leading end of the connection portion 93 can be inserted, for example. The connection portion 93 is disposed in the hole portion 96b1, and the peripheral region of the hole portion 96b1 is welded to the connection portion 93 using heat. The sixth sheet member 96b is joined to the inner circumferential surface of the back plate 72 with the joining layer 75 in between.

The tensile cuff 74 is fluidly connected to the pump 14 through the flow path portion 15. The tensile cuff 74 is inflated to press the curler 5 such that the curler 5 is spaced apart from the wrist 200, pulling the belt 4 and the curler 5 toward the backhand side of the wrist 200. The tensile cuff 74 includes a plurality of, for example, six-layer air bags 101, a target join portion 102 provided on the air bag 101 facing the curler 5, the connection portion 103 provided on the air bag 101 facing the curler 5, and a cutout portion 104 provided on at least the air bag 101 facing the curler 5. The tensile cuff 74 with such a configuration is constituted by welding a plurality of sheet members 106. In addition, the tensile cuff 74 is fixed to the region where the flow path bodies 83 and 92 are provided and the curler 5, including the cover portion 5a, on the backhand side of the wrist 200. In other words, the flow path body 83 of the pressing cuff 71 and the flow path body 92 of the sensing cuff 73 are disposed between the curler 5 on the backhand side of the wrist 200 and the tensile cuff 74.

Additionally, the tensile cuff 74 is configured such that the thickness of the tensile cuff 74 in an inflating direction, in the present embodiment, in the direction in which the curler 5 and the wrist 200 face each other, during inflation, is larger than the thickness of the pressing cuff 71 in the inflating direction during inflation and than the thickness of the sensing cuff 73 in the inflating direction during inflation. Specifically, the air bags 101 of the tensile cuff 74 include more layer structures than the air bags 81 in the pressing cuff 71 and the air bag 91 in the sensing cuff 73, and have thicker thickness than the pressing cuff 71 and the sensing cuff 73 when the air bags 101 are inflated from the curler 5 toward the wrist 200.

In the present embodiment, the tensile cuff 74 including the six-layer air bags 101 includes a first outer layer 111 constituted by one air bag 101, a first intermediate layer 112 constituted by two-layer air bags 101 integrally combining with the first outer layer 111 by welding using heat, a second intermediate layer 113 constituted by two-layer air bags 101 integrally combining with the first intermediate layer 112 by welding using heat, and a second outer layer 114 constituted by one air bag 101 integrally combining with the second intermediate layer 113 by welding using heat.

Here, the air bags 101 are bag-like structures, and in the present embodiment, the blood pressure measurement device 1 is configured to use air with the pump 14, and thus the present embodiment will be described using the air bags. However, in a case where a fluid other than air is used, the bag-like structures may be fluid bags that are inflated by a fluid. A plurality of the air bags 101 are stacked and are in fluid communication in the stacking direction.

Each of the air bags 101 is formed in a rectangular bag-like shape that is long in one direction. Additionally, the air bags 101 are set so that the width in the lateral direction is the same as the width in the lateral direction of the curler 5. The air bags 101 are each constituted by, for example, combining two sheet members 106 and, as illustrated in FIGS. 13, 14, 16, and 17, welding a weld portion 101a using heat into a rectangular frame shape long in one direction. The six-layer air bags 101 are fluidly continuous through openings provided in the sheet members 106 facing one another.

In addition, in the six-layer air bags 101, for the first outer layer 111 and the first intermediate layer 112, the first intermediate layer 112 and the second intermediate layer 113, and the second intermediate layer 113 and the second outer layer 114, by bridge welding the opposing sheet members 106 together with a quadrilateral frame shape smaller than the weld portion 81*a* located on the outer peripheral edge and surrounding the plurality of openings with the bridge weld portion (join portion) 101*b*, the adjacent air bags 101 are integrally formed and made fluidly continuous on the inner side of the bridge weld portion 101*b*.

The first outer layer 111 is formed by one air bag 101 disposed on the wrist 200 side. The first outer layer 111 constitutes the first air bag 101 of the six-layer air bags 101 from the wrist 200 side.

The first intermediate layer 112 is stacked on the first outer layer 111. The first intermediate layer 112 is formed by two-layer air bags 101. The first intermediate layer 112 constitutes the second and third air bags 101 of the six-layer air bags 101 from the wrist 200 side. The first intermediate layer 112 is constituted by two-layer air bags 101 integrally welded at the outer peripheral edge. In other words, the first intermediate layer 112 is formed by integrally welding four sheet members 106 in the outer peripheral edge shape of the air bags 101.

The second intermediate layer 113 is stacked on the first intermediate layer 112. The second intermediate layer 113 is formed by two-layer air bags 101. The second intermediate layer 113 constitutes the fourth and fifth air bags 101 of the six-layer air bags 101 from the wrist 200 side. The second intermediate layer 113 is constituted by two-layer air bags 101 integrally welded at the outer peripheral edge. In other words, the second intermediate layer 113 is formed by integrally welding four sheet members 106 in the outer peripheral edge shape of the air bags 101.

The second outer layer 114 is formed by one air bag 101 disposed on the curler 5 side. The second outer layer 114 constitutes the sixth air bag 101 of the six-layer air bags 101 from the wrist 200 side.

A single or a plurality of target join portions 102 are provided at at least a portion of the edge portion of the air bag (the sixth air bag) 101 disposed adjacent to the curler 5. The target join portion 102 is formed by a portion of the sheet member 106 forming the air bag 101.

An example of the present embodiment will be described using examples in which two target join portions 102 are each provided in the longitudinal direction of the air bags 101 on the edge portion in the lateral direction of each of the air bags 101. Note that, for example, the target join portions 102 are provided on the air bags 101 avoiding the positions facing the cover portion 5*a* of the curler 5. Furthermore, for example, the target join portion 102 includes an escape portion 102*a*, which is for externally exposing a power feeding terminal 8*b* described below of the power feeding unit 8 provided on the curler 5, at a portion facing the power feeding terminal 8*b*. The escape portion 102*a*, for example, is an opening through which the power feeding terminal 8*b* can be externally exposed and has a circular shape as an example.

The target join portion 102 is at least joined to the outer circumferential surface of the curler 5 when the tensile cuff 74 is disposed on the inner circumferential surface of the curler 5. Additionally, the target join portions 102 disposed at the same position in the lateral direction of the air bags 101 are stacked and welded.

Note that the two target join portions 102 are set to have a different length to the length in the lateral direction of the air bags 101, for example. In this example, the two target join portions 102 are stacked and welded at the first end side in the lateral direction of the curler 5. Note that as long as the two target join portions 102 are able to be disposed with the leading end on the outer circumferential surface of the curler 5, the length is able to be set as appropriate and the two target join portions 102 may be stackable or not. However, in a case where the length is set to a stackable length, the length is preferably a length such that the leading end does not extend further out than the outer edge of the outer circumferential surface of the curler 5.

The connection portion 103 is, for example, a nipple. The connection portion 103 is provided at a position facing the third hole portion 5*f*3 of the cover portion 5*a* in a central region in the longitudinal direction of the air bag 101 disposed adjacent to the curler 5. The leading end of the connection portion 103 is exposed from the sheet member 106 facing the curler 5, of the two sheet members 106 forming the air bag 101. The connection portion 103 is inserted in the third hole portion 5*f*3 of the cover portion 5*a* and is connected to the flow path portion 15.

The cutout portion 104 is provided at a position facing the escape portion 5*b* provided on the curler 5. The cutout portion 104 is provided on the sixth air bag 101 forming the second outer layer 114.

In a specific example, as illustrated in FIGS. 13, and 14, the tensile cuff 74 includes a seventh sheet member 106*a*, an eighth sheet member 106*b*, a ninth sheet member 106*c*, a tenth sheet member 106*d*, an eleventh sheet member 106*e*, a twelfth sheet member 106*f*, a thirteenth sheet member 106*g*, a fourteenth sheet member 106*h*, a fifteenth sheet member 106*i*, a sixteenth sheet member 106*j*, a seventeenth sheet member 106*k*, and an eighteenth sheet member 106*l* in this order from the wrist 200 side. Note that the tensile cuff 74 is integrally constituted by joining adjacent sheet members 106 by welding using heat.

The seventh sheet member 106*a* to the eighteenth sheet member 106*l* are constituted in a similar rectangular shape to the air bags 101. The seventh sheet member 106*a* and the eighth sheet member 106*b* are welded using heat along the peripheral edge portion shape on the four sides of the air bags 101 to constitute the first (first layer) air bag 101 from the wrist 200 side. In other words, the seventh sheet member 106*a* and the eighth sheet member 106*b* constitute the first outer layer 111.

The eighth sheet member 106*b* and the ninth sheet member 106*c* are disposed facing each other, and each includes a plurality of openings 106*b*1 and 106*c*1 through which the two air bags 101 are fluidly continuous. Additionally, the eighth sheet member 106*b* and the ninth sheet member 106*c* are integrally joined by the peripheral region of the plurality of openings 106*b*1 and 106*c*1 being bridge welded using heat in a quadrilateral frame shape smaller than the welded four sides of the air bags 101.

The ninth sheet member 106*c* and the tenth sheet member 106*d* are welded using heat along the peripheral edge portion shape on the four sides of the air bags 101 to constitute the second (second layer) air bag 101 from the wrist 200 side.

As illustrated in FIGS. 13 and 14, the tenth sheet member 106*d* and the eleventh sheet member 106*e* include a plurality of openings 106*d*1 and 106*e*1 disposed facing one another and through which the two air bags 101 are fluidly continuous. The eleventh sheet member 106*e* and the twelfth sheet member 106*f* are welded using heat along the peripheral edge portion shape on the four sides of the air bags 101 to constitute the third (third layer) air bag 101 from the wrist 200 side.

The ninth sheet member 106*c*, the tenth sheet member 106*d*, the eleventh sheet member 106*e*, and the twelfth sheet member 106*f* are integrally welded using heat along the peripheral edge portion shape on the four sides of the air bags 101 to constitute the first intermediate layer 112 in which the second and third air bags 101 are integrally formed.

As illustrated in FIGS. 13 and 14, the twelfth sheet member 106f and the thirteenth sheet member 106g include a plurality of openings 106f1 and 106g1 disposed facing one another and through which the two air bags 101 are fluidly continuous. Additionally, the twelfth sheet member 106f and the thirteenth sheet member 106g are integrally joined by the peripheral region of the plurality of openings 106f1 and 106g1 being bridge welded using heat in a quadrilateral frame shape smaller than the welded four sides of the air bags 101.

The thirteenth sheet member 106g and the fourteenth sheet member 106h are welded using heat along the peripheral edge portion shape on the four sides of the air bags 101 to constitute the fourth (fourth layer) air bag 101 from the wrist 200 side.

As illustrated in FIGS. 13 and 14, the fourteenth sheet member 106h and the fifteenth sheet member 106i include a plurality of openings 106h1 and 106i1 disposed facing one another and through which the two air bags 101 are fluidly continuous. The fifteenth sheet member 106i and the sixteenth sheet member 106j are welded using heat along the peripheral edge portion shape on the four sides of the air bags 101 to constitute the fifth (fifth layer) air bag 101 from the wrist 200 side.

The thirteenth sheet member 106g, the fourteenth sheet member 106h, the fifteenth sheet member 106i, and the sixteenth sheet member 106j are integrally welded using heat along the peripheral edge portion shape on the four sides of the air bags 101 to constitute the second intermediate layer 113 in which the fourth and fifth air bags 101 are integrally formed.

As illustrated in FIGS. 13 and 14, the sixteenth sheet member 106j and the seventeenth sheet member 106k include a plurality of openings 106j1 and 106k1 disposed facing one another and through which the two air bags 101 are fluidly continuous. Also, the seventeenth sheet member 106k, for example, is constituted in a shape that allows the air bag 101 and the target join portion 102 to be constituted. Additionally, the sixteenth sheet member 106j and the seventeenth sheet member 106k are integrally joined by the peripheral region of the plurality of openings 106j1 and 106k1 being bridge welded using heat in a quadrilateral frame shape smaller than the welded four sides of the air bags 101.

The seventeenth sheet member 106k and the eighteenth sheet member 106l are welded using heat along the peripheral edge portion shape on the four sides of the air bag 101 and cut in a predetermined shape to constitute the sixth air bag 101 from the wrist 200 side, which includes the cutout portion 104, and the target join portion 102.

Furthermore, the eighteenth sheet member 106l includes a hole portion 106l1 into which the leading end of the connection portion 103 can be inserted, for example. The eighteenth sheet member 106l is disposed with the connection portion 103 at the hole portion 106l1, and the peripheral region of the hole portion 106l1 is welded to the connection portion 103 using heat. Furthermore, the eighteenth sheet member 106l is joined with the inner circumferential surface of the curler 5 with the joining layer 75 in between, and the target join portion 102 of the seventeenth sheet member 106k is joined to the outer circumferential surface of the curler 5 with the joining layer 75 in between.

Additionally, each of the sheet members 86, 96, and 106 forming the pressing cuff 71, the sensing cuff 73, and the tensile cuff 74 are formed of a thermoplastic resin material. The thermoplastic resin material is a thermoplastic elastomer. Examples of thermoplastic resin material constituting the sheet members 86, 96, and 106 include thermoplastic polyurethane based resin (hereinafter referred to as TPU), polyvinyl chloride resin, ethylene-vinyl acetate resin, thermoplastic polystyrene based resin, thermoplastic polyolefin resin, thermoplastic polyester based resin, and thermoplastic polyamide resin. Note that, in the pressing cuff 71 and the sensing cuff 73, of at least the plurality of sheet members 86 and 106 constituting the air bags 81 and 101, at least the sheet members 86 and 106 welded to the curler 5 are constituted by a material similar to the material of the curler 5.

For example, the sheet members 86, 96, and 106 are formed using a molding method such as T-die extrusion molding or injection molding. After being molded by each molding method, the sheet members 86, 96, and 106 are sized into predetermined shapes, and the sized individual pieces are joined by welding or the like to constitute bag-like structures 81, 91, and 101. A high frequency welder or laser welding is used as the welding method.

The fluid circuit 7 is constituted by the case 11, the pump 14, the flow path portion 15, the on-off valves 16, the pressure sensors 17, the pressing cuff 71, the sensing cuff 73, and the tensile cuff 74. A specific example of the fluid circuit 7 will be described below.

As illustrated in FIG. 7, for example, the fluid circuit 7 includes a first flow path 7a in which the pump 14, the sensing cuff 73, the first pressure sensor 17A and the second pressure sensor 17B are continuous through the first on-off valve 16A, a second flow path 7b which is constituted by branching from the first flow path 7a between the pump 14 and the first on-off valve 16A and is continuous from the pump 14 to the atmosphere through the second on-off valve 16B, the third on-off valve 16C, and the fourth on-off valve 16D sequentially in this order, a third flow path 7c which is constituted by branching from an intermediate portion of the second flow path 7b between the second on-off valve 16B and the third on-off valve 16C and is continuous from the pump 14 to the tensile cuff 74, and a fourth flow path 7d which is constituted by branching from an intermediate portion of the second flow path 7b between the third on-off valve 16C and the fourth on-off valve 16D and is continuous from the pump 14 to the pressing cuff 71.

In the fluid circuit 7 with such a configuration, by the second on-off valve 16B and the third on-off valve 16C being open and the first on-off valve 16A and the fourth on-off valve 16D being closed, the third flow path 7c and the fourth flow path 7d branching from the second flow path 7b are connected to the pump 14, and the pump 14, the pressing cuff 71, and the tensile cuff 74 are fluidly connected.

In the fluid circuit 7, by the first on-off valve 16A, the second on-off valve 16B, and the third on-off valve 16C being open and the fourth on-off valve 16D being closed, the first flow path 7a and the third flow path 7c and the fourth flow path 7d branching from the second flow path 7b are connected to the pump 14, and the pump 14, the pressing cuff 71, and the tensile cuff 74 and the pump 14 and the sensing cuff 73 are fluidly connected. In the fluid circuit 7, by the second on-off valve 16B, the third on-off valve 16C, and the fourth on-off valve 16D being open and the first on-off valve 16A being closed, the second flow path 7b, the third flow path 7c, and the fourth flow path 7d are connected to the pump 14, and the pump 14, the pressing cuff 71, the tensile cuff 74, and the atmosphere are fluidly connected. In the fluid circuit 7, by the first on-off valve 16A, the second on-off valve 16B, the third on-off valve 16C, and the fourth on-off valve 16D being open, the first flow path 7*a*, the second flow path 7*b*, the third flow path 7*c*, and the fourth flow path 7*d* are connected to the pump 14, and the pump 14, the pressing cuff 71, the sensing cuff 73, the tensile cuff 74, and the atmosphere are fluidly connected.

As illustrated in FIGS. 8 to 10, the power feeding unit 8 is provided in the recess 5*c* formed in the outer surface of the curler 5 on the first end side that projects from the device body 3. For example, the power feeding unit 8 is configured to be capable to connect to a connector provided on a charging cable of a charger.

As illustrated in FIGS. 3, and 8 to 10, the power feeding unit 8 is provided with a wiring portion 8*a*, the power feeding terminal 8*b*, and a cover 8*c* that covers the wiring portion 8*a* disposed in the recess 5*c* of the curler 5. The first end of the wiring portion 8*a* is connected to the power feeding terminal 8*b*, and the second end is connected to the control unit 55. The power feeding terminal 8*b* is constituted by two circular terminals, for example. For example, the wiring portion 8*a* and the power feeding terminal 8*b* are formed of flexible printed circuits (FPC) and the like including a base film, such as polyimide, provided with an electrically conductive metal film and the like. The cover 8*c* is formed in the same shape as the recess 5*c* and covering the recess 5*c*, and the upper surface runs flush with the outer surface of the curler 5 on the shorter side when the cover 8*c* is provided in the recess 5*c*.

As illustrated in FIG. 22, the cover 9 includes a bag body 121 long in one direction, a first hole portion 122 provided in the bag body 121, and a second hole portion 123 provided in the bag body 121. The cover 9 covers the curler 5 and the cuff structure 6 to protect the curler 5 and the cuff structure 6.

The bag body 121 is formed in a rectangular bag-like shape that is long in one direction. A portion of the bag body 121 that faces the cuff structure 6 has higher stretchability than a portion facing the outer circumferential surface of the curler 5, and the bag body 121 has stretchability such that the expansion of the cuff structure 6 is not hindered. Here, stretchability such that the expansion of the cuff structure 6 is not hindered refers stretchability that, when the blood pressure is measured using the blood pressure measurement device 1, allows for a suitable blood pressure measurement to be performed or, in other words, stretchability such that a decrease to an accuracy not suitable for blood pressure measurement is prevented while maintaining the blood pressure measurement accuracy of the blood pressure measurement device 1 within a predetermined range. The stretchability of the bag body 121 is set as appropriate depending on the configuration and design values such as dimensions of the cuff structure 6, the performance of the pump 14, other conditions and the like.

The internal dimensions of the bag body 121 in the longitudinal direction are set to equal to or greater than the length of the curler 5 in the circumferential direction (longitudinal direction). The internal dimensions of the bag body 121 in the lateral direction is set to equal to or greater than the width of the curler 5 in the lateral direction, and preferably set to greater than the width of the curler 5 in the lateral direction.

As illustrated in FIGS. 23 to 26, the bag body 121 includes the single cloth 131 with a rectangular shape and the weld sheet 132. As a fold line 131*a* illustrated by a two-dot chain line in FIG. 23, an edge portion on the direction orthogonal to the longitudinal direction of the single cloth 131 is folded along a longitudinal edge portion of the bag body 121 in a valley folding direction. Then, as illustrated in FIGS. and 26, the bag body 121 is constituted such that two portions of the folded cloth 131 are partially overlapped with the weld sheet 132 disposed therebetween, and the overlapped cloth 131 are welded together by the weld sheet 132.

The first hole portion 122 is formed in a shape such that the curler 5 and the cuff structure 6 are insertable inside the bag body 121 by elongating the bag body 121 when the curler 5 and the cuff structure 6 are inserted inside the bag body 121. For example, as illustrated in FIG. 22, the first hole portion 122 is an opening that extends in the longitudinal direction of the bag body 121 or a slit-like opening.

As illustrated in FIG. 8, the second hole portion 123 is formed to allow the power feeding terminals 8*b* of the power feeding unit 8 provided on the curler 5 and the regions around the two power feeding terminals 8*b* to be exposed to the outside when the bag body 121 covers the curler 5 and the cuff structure 6. For example, as illustrated in FIG. 22, the second hole portion 123 is formed in a circular shape that allows the two power feeding terminals 8*b* to be disposed.

In the single rectangular cloth 131, the dimension in one direction is set to be greater than the sum of a dimension double the width of the curler 5 in the lateral direction and a dimension of the first hole portion 122 in the same direction, and is set to be 3 times or less the width of the curler 5 in the lateral direction. In addition, the dimension of the single cloth 131 in the direction orthogonal to the one direction is set to be greater than the sum of a dimension of the curler 5 in the circumferential direction and a dimension of the weld margin on both end portions of the longitudinal direction of the bag body 121.

The weld sheet 132 is formed in the shape of the region where the single cloth 131 is welded. The weld sheet 132 is a so-called hot melt film and is heated so as to fix the cloth 131.

Next, as illustrated in FIG. 27, an example of the method for manufacturing the cover 9 will be described.

First, as illustrated in FIG. 27, the weld sheet 132 is disposed to stack on the portion of the cloth 131 that is to be welded (step ST11). Next, the stacked cloth 131 and the weld sheet 132 are folded (step ST12) as illustrated in FIGS. 25 and 26.

Specifically, both end portions of the cloth 131 in one direction are folded back to overlap the end portions together. The overlapped end portions constitute a portion facing the outer circumferential surface of the curler 5. In addition, the weld sheet 132 is disposed between two layers of the cloth 131 where the end portions of the folded cloth 131 are present. In addition, the folded cloth 131 has a long shape in one direction.

Next, for example, as a first weld, the two layers of the cloth 131 disposed with the weld sheet 132 in between are sandwiched in a mold, and the two layers of the cloth 131 are welded by the weld sheet 132 (step ST13). This gives the cloth 131 a shape that is long in one direction and has both ends in the longitudinal direction open. Next, the first hole portion 122 and the second hole portion 123 are cut in the welded portion of the two layers of the cloth 131 (step ST14). In a specific example, the first hole portion 122 and the second hole portion 123 are punched out by a press machine.

Next, as a second weld, both ends in the longitudinal direction of the cloth 131 are sandwiched in a mold and welded by the weld sheet 132 (step ST15). Next, as a finishing cut, both welded end portions are cut (step ST16). With these processes, the cover 9 is manufactured.

An example of a procedure of attaching the cover 9 to the curler 5 and the cuff structure 6 will now be described. First, the peripheral region of the first hole portion 122 is pinched by fingers of both hands, and the first hole portion 122 is expanded. Then, the curler 5 is inserted into the first hole portion 122 from the end portion on the longitudinal side of the curler 5. Note that at this time, the curler 5 is inserted inside the bag body 121 from the first hole portion 122 with the outer circumferential surface side of the curler 5 positioned on the first hole portion 122 side of the bag body 121. When the curler 5 has been inserted and passed the cover portion 5a to the longer side, the end portion of the bag body 121 on the side where the curler 5 is not disposed is pulled to stretch the first hole portion 122, and the end portion of the shorter side of the curler 5 is inserted from the first hole portion 122. In this manner, the shorter side and the longer side portions of the curler 5, excluding the cover portion 5a, are disposed inside the cover 9. Note that, by attaching the cover 9 to the curler 5, the second hole portion 123 of the cover 9 is positioned so as to face the power feeding terminals 8b of the power feeding unit 8 provided on the curler 5, exposing the power feeding terminals 8b to the outside.

Next, an example of measurement of a blood pressure value using the blood pressure measurement device 1 will be described using FIGS. 28 to 31. FIG. 28 is a flowchart illustrating an example of a blood pressure measurement using the blood pressure measurement device 1, illustrating both an operation of a user and an operation of the control unit 55. Additionally, FIGS. 29 to 31 illustrate an example of the user attaching the blood pressure measurement device 1 on the wrist 200.

Note that when the user uses the blood pressure measurement device 1, the cover 9 is attached to the curler 5 and the cuff structure 6 in advance. First, the user attaches the blood pressure measurement device 1 to the wrist 200 (step ST21). As a specific example, for example, the user inserts one of the wrists 200 into the curler 5, as illustrated in FIG. 29.

At this time, in the blood pressure measurement device 1, the device body 3 and the sensing cuff 73 are disposed at opposite positions in the curler 5, and thus the sensing cuff 73 is disposed in a region on the hand palm-side of the wrist 200 in which the artery 210 resides. Thus, the device body 3 and the tensile cuff 74 are disposed on the backhand side of the wrist 200. Then, as illustrated in FIG. 30, the user passes the second belt 62 through the frame body 61e of the buckle 61b of the first belt 61 with the hand opposite to the hand on which the blood pressure measurement device 1 is disposed. The user then pulls the second belt 62 to bring the member on the inner circumferential surface side of the curler 5, that is, the cuff structure 6, into close contact with the wrist 200, and inserts the prong 61f into one of the small holes 62a. Thus, as illustrated in FIGS. 6 and 32, the first belt 61 and the second belt 62 are connected, and the blood pressure measurement device 1 is attached to the wrist 200.

Next, the user operates the operation unit 13 and inputs an instruction corresponding to the start of measurement of the blood pressure value. The operation unit 13, on which an input operation of the instruction has been performed, outputs an electrical signal corresponding to the start of the measurement to the control unit 55 (step ST22). The control unit 55 receives the electrical signal, and then for example, opens the first on-off valve 16A, the second on-off valve 16B, and the third on-off valve 16C, closes the fourth on-off valve 16D, and drives the pump 14 to supply compressed air to the pressing cuff 71, the sensing cuff 73, and the tensile cuff 74 through the first flow path 7a, the second flow path 7b, the third flow path 7c, and the fourth flow path 7d (step ST23). Thus, the pressing cuff 71, the sensing cuff 73, and the tensile cuff 74 start to be inflated.

The first pressure sensor 17A and the second pressure sensor 17B detect the pressures in the pressing cuff 71, the sensing cuff 73, and the tensile cuff 74, and output, to the control unit 55, electrical signals corresponding to the pressures (step ST24). On the basis of the received electrical signals, the control unit 55 determines whether the pressures in the internal spaces of the pressing cuff 71, the sensing cuff 73, and the tensile cuff 74 have reached a predetermined pressure for measurement of the blood pressure (step ST25). For example, in a case where the internal pressures of the pressing cuff 71 and the tensile cuff 74 have not reached the predetermined pressure and the internal pressure of the sensing cuff 73 has reached the predetermined pressure, the control unit 55 closes the first on-off valve 16A and supplies the compressed air through the second flow path 7b, the third flow path 7c, and the fourth flow path 7d.

When the internal pressures of the pressing cuff 71 and the tensile cuff 74 and the internal pressure of the sensing cuff 73 all have reached the predetermined pressure, the control unit 55 stops driving the pump 14 (YES in step ST25). At this time, as illustrated by the two-dot chain line in FIG. 6, the pressing cuff 71 and the tensile cuff 74 are sufficiently inflated, and the inflated pressing cuff 71 presses the back plate 72. Additionally, the tensile cuff 74 presses against the curler 5 in a direction away from the wrist 200, and then the belt 4, the curler 5, and the device body 3 move in a direction away from the wrist 200, and as a result, the pressing cuff 71, the back plate 72, and the sensing cuff 73 are pulled toward the wrist 200 side. In addition, when the belt 4, the curler 5, and the device body 3 move in a direction away from the wrist 200 due to the inflation of the tensile cuff 74, the belt 4 and the curler 5 move toward both lateral sides of the wrist 200, and the belt 4, the curler 5, and the device body 3 move in a state of close contact with both lateral sides of the wrist 200. Thus, the belt 4 and the curler 5, which are in close contact with the skin of the wrist 200, pull the skin on both lateral sides of the wrist 200 toward the backhand side. Note that the curler 5 may be configured to indirectly contact the skin of the wrist 200 with the sheet members 86 or 106 in between, for example, as long as the curler 5 can pull the skin of the wrist 200.

Furthermore, the sensing cuff 73 is inflated by being supplied with a predetermined amount of air such that the internal pressure equals the pressure required to measure blood pressure, and is pressed toward the wrist 200 by the back plate 72 that is pressed by the pressing cuff 71. Thus, the sensing cuff 73 presses the artery 210 in the wrist 200 and occludes the artery 210 as illustrated in FIG. 32.

Additionally, the control unit 55, for example, controls the third on-off valve 16C and repeats the opening and closing of the third on-off valve 16C, or adjusts the degree of opening of the third on-off valve 16C to pressurize a pressure of the internal space of the pressing cuff 71. In the process of pressurization, based on the electrical signal output by the second pressure sensor 17B, the control unit 55 obtains measurement results such as blood pressure values, for example, the systolic blood pressure and the diastolic blood pressure, and the heart rate and the like (step ST26). The control unit 55 outputs an image signal corresponding to the obtained measurement results to the display unit 12, and displays the measurement results on the display unit 12 (step ST27). In addition, after the end of the blood pressure measurement, the control unit 55 opens the first on-off valve 16A, the second on-off valve 16B, the third on-off valve 16C, and the fourth on-off valve 16D.

The display unit 12 receives the image signal, and then displays the measurement results on the screen. The user views the display unit 12 to confirm the measurement results. After the measurement is complete, the user removes the prong 61f from the small hole 62a, removes the second belt 62 from the frame body 61e, and pulls out the wrist 200 from the curler 5, thus detaching the blood pressure measurement device 1 from the wrist 200.

The cover 9 attached to the blood pressure measurement device 1 according to an embodiment with the configuration described above is configured to be stretchable and to include the bag body 121 with a length that allows the curler 5 to be disposed and the first hole portion 122 into which the curler 5 can be inserted. By the cover 9 being elongated, the curler 5 can be inserted from the first hole portion 122 and, when the cover 9 is attached to the curler 5, the cover 9 can cover the outer circumferential surface of the curler 5 excluding the cover portion 5a. Thus, the cover 9 can prevent the curler 5 and the cuff structure 6 from becoming dirty. Also, because the cover 9 is disposed between the wrist 200 and the cuff structure 6, the feel on the skin is good, and by forming of the cloth 131, the contact portion does not become stuffy. And thus, the wearability of the blood pressure measurement device can be improved.

Also, because the bag body 121 has a stretchable configuration, the bag body 121 stretches following to the expansion of the cuff structure 6, and thus the expansion of the cuff structure 6 is not hindered. This allows the cover 9 to cover the curler 5 and the cuff structure 6 without reducing the blood pressure measurement accuracy of the blood pressure measurement device 1. Also, because the peripheral region of the first hole portion 122 can be stretched, the curler 5 and the cuff structure 6 can be disposed inside the bag body 121. This allows the cover 9 to be easily attached to the curler 5 and cuff structure 6.

In addition, the bag body 121 is constituted by the single cloth 131 with both ends folded back at a portion facing the outer circumferential surface of the curler 5 and stacked, and the weld sheet 132 for welding the cloth 131 provided on the stacked portion of the cloth 131 and both ends in the longitudinal direction of the bag body 121. In this manner, the bag body 121 can be constituted by welding the single cloth 131 into a bag-like shape using the weld sheet 132, making manufacture simple. In addition, in the bag body 121, the weld sheet 132 is disposed at a portion facing the outer circumferential surface of the curler 5, and thus the cover 9 has flexibility and stretchability at the portion facing the outer circumferential surface of the curler 5 than at the portion facing the inner circumferential surface of the curler 5.

Thus, the portion of the cover 9 provided with the weld sheet 132 facing the outer circumferential surface side of the curler 5 maintains its shape. And thus when the cover 9 is attached to the curler 5, misalignment of the curler 5 in the lateral direction can be prevented. In addition, the portion of the cover 9 constituted only by the cloth 131 that faces the inner circumferential surface side of the curler 5 is more flexible and stretchable than the portion facing the outer circumferential surface side of the curler 5. This ensures that the expansion of the cuff structure 6 is not hindered. Thus, the cover 9 can be easily manufactured, does not reduce the blood pressure measurement accuracy of the blood pressure measurement device 1, and can prevent misalignment of the cover 9 when the blood pressure measurement device 1 is in use.

Additionally, the bag body 121 is formed such that the internal width in the lateral direction is greater than the width in the lateral direction of the curler 5. And thus when the cover 9 is attached to the curler 5 and the cuff structure 6, it is possible to secure a stretching margin of the bag body 121 when the cuff structure 6 is inflated. In this manner, the cover 9 can suppress pressing on the cuff structure 6 in the direction facing the direction in which the cuff structure 6 expands when the bag body 121 is elongated. As a result, the cover 9 can cover the curler 5 and cuff structure 6 without hindering the expansion of the cuff structure 6.

In addition, the first hole portion 122 into which the curler 5 is inserted and the second hole portion 123 that exposes the power feeding terminals 8b are provided at a portion where two end portions of the cloth 131 and the weld sheet 132 are stacked. This portion is formed by the two layers of the cloth 131 and the weld sheet 132, and thus, is a region of high strength in the bag body 121.

Thus, the strength in the peripheral region of the opening of the first hole portion 122 can be improved while keeping stretchability. Accordingly, damage can be prevented even when the first hole portion 122 is repeatedly stretched when the curler 5 and the cuff structure 6 are inserted. As a result, the cover 9 can be used repeatedly. Similarly, the second hole portion 123 that exposes the power feeding terminals 8b is provided at a portion of the bag body 121 which is formed by the two layers of the cloth 131 and the weld sheet 132. Accordingly, the strength in the peripheral region of the opening of the second hole portion 123 can be improved while keeping stretchability. Thus, damage can be prevented even when an external force is applied by the connector when the connector that connects with the power feeding unit 8 is repeatedly attached and detached to and from the power feeding terminals 8b of the power feeding unit 8.

As described above, according to the cover 9 used in the blood pressure measurement device 1 according to the present embodiment, the measurement accuracy of the blood pressure measurement device 1 is not reduced, and the curler 5 and the cuff structure 6 can be easily covered.

Note that the present invention is not limited to the embodiments described above. An example of the method for manufacturing the cover 9 has been described above, but no such limitation is intended. For example, in the example described above, a configuration has been described in which the first hole portion 122 and the second hole portion 123 are cut after the rectangular cloth 131 and the weld sheet 132 are stacked and the first weld is performed. Also, for example, holes that constitute the first hole portion 122 and the second hole portion 123 may be provided in each end portions of the cloth 131, which will be stacked, and the weld sheet 132, and then the first hole portion 122 and the second hole portion 123 may be formed by overlaying both ends of the cloth 131 and the weld sheet 132.

That is, the present invention is not limited to the embodiments described above, and various modifications can be made in an implementation stage within a range that does not depart from the gist of the present invention. Furthermore, each of the embodiments may be implemented in combination as appropriate to the extent possible, and in this case, combined effects can be obtained. Also, the embodiments described above include various stages of invention, and various inventions may be extracted by appropriately combining the described plurality of disclosed constituent elements.

REFERENCE SIGNS LIST

1 Blood pressure measurement device
3 Device body

4 Belt
5 Curler
5a Cover portion
5b Escape portion
5c Recess
5d Insert member
5e Screw hole
5f Hole portion
5f1 First hole portion
5f2 Second hole portion
5f3 Third hole portion
6 Cuff structure
7 Fluid circuit
7a First flow path
7b Second flow path
7c Third flow path
7d Fourth flow path
8 Power feeding unit
8a Wiring portion
8b Power feeding terminal
8c Cover
9 Cover (cuff cover for blood pressure measurement device)
11 Case
12 Display unit
13 Operation unit
14 Pump
15 Flow path portion
16 On-off valve
16A First on-off valve
16B Second on-off valve
16C Third on-off valve
16D Fourth on-off valve
17 Pressure sensor
17A First pressure sensor
17B Second pressure sensor
18 Power supply unit
19 Vibration motor
20 Control substrate
31 Outer case
31a Lug
31b Spring rod
32 Windshield
33 Base
35 Rear cover
35a First joining member
35b Second joining member
35c Hole portion
35d Hole portion
36 Sealing member
41 Button
42 Sensor
43 Touch panel
51 Substrate
52 Acceleration sensor
53 Communication unit
54 Storage unit
55 Control unit
56 Main CPU
57 Sub-CPU
61 First belt
61a Belt portion
61b Buckle
61c First hole portion
61d Second hole portion
61e Frame body
61f Prong
62 Second belt
62a Small hole
62b Third hole portion
71 pressing cuff
72 Back plate
72a Groove
73 Sensing cuff
74 Tensile cuff
75 Joining layer
81 Air bag (bag-like structure)
81a Weld portion
81b Bridge weld portion
82 Target join portion
83 Flow path body
83a Weld portion
84 Connection portion
86 Sheet member
86a First sheet member
86b Second sheet member
86b1 Opening
86c Third sheet member
86c1 Opening
86d Fourth sheet member
86d1 Hole portion
91 Air bag (bag-like structure)
91a Weld portion
91b Junction margin
92 Flow path body
92a Weld portion
93 Connection portion
96 Sheet member
96a Fifth sheet member
96b Sixth sheet member
96b1 Hole portion
101 Air bag (bag-like structure)
101a Weld portion
101b Bridge weld portion
102 Target join portion
102a Escape portion
103 Connection portion
104 Cutout portion
106 Sheet member
106a Seventh sheet member
106b Eighth sheet member
106b1 Opening
106c Ninth sheet member
106c1 Opening
106d Tenth sheet member
106d1 Opening
106e Eleventh sheet member
106e1 Opening
106f Twelfth sheet member
106f1 Opening
106g Thirteenth sheet member
106g1 Opening
106h Fourteenth sheet member
106h1 Opening
106i Fifteenth sheet member
106i1 Opening
106j Sixteenth sheet member
106j1 Opening
106k Seventeenth sheet member
106k1 Opening
106l Eighteenth sheet member
106l1 Hole portion
111 First outer layer
112 First intermediate layer
113 Second intermediate layer 114 Second outer layer
121 Bag body
122 First hole portion
123 Second hole portion
131 Cloth
131a Fold line
132 Weld sheet
200 Wrist
210 Artery

The invention claimed is:

1. A cuff cover for a blood pressure measurement device attachable to a wrist, the cuff cover comprising:
a bag body having a stretchable bag shape long in one direction with a length that allows a cuff structure and a curler curving and following along a shape of the wrist to be disposed inside the bag body, the cuff structure being provided on an inner circumferential surface of the curler, a device body being disposed on a portion of an outer circumferential surface of the curler, and a power feeding terminal being provided at a position on the outer circumferential surface of the curler adjacent to the device body;
a first hole portion extending in a longitudinal direction of the bag body, and provided at a portion of the bag body facing the outer circumferential surface of the curler, the device body being configured to be disposed at the portion, the first hole portion being configured to allow the curler provided with the cuff structure to be inserted by elongating the bag body; and
a second hole portion formed in a shape allowing the power feeding terminal to be exposed, the second hole portion being provided at a portion of the bag body facing the power feeding terminal provided on the outer circumferential surface of the curler,
wherein the first hole portion is configured to connect the portion of the outer circumferential surface of the curler and the device body disposed outside the bag body.

2. The cuff cover for a blood pressure measurement device according to claim 1, wherein the bag body includes a single cloth that is stacked at a portion facing the outer circumferential surface of the curler, and a weld sheet, for welding the cloth, provided at both ends in the longitudinal direction of the bag body and at the portion of the cloth to be stacked.

3. The cuff cover for a blood pressure measurement device according to claim 2, wherein the first hole portion and the second hole portion are provided at the portion of the cloth to be stacked.

4. The cuff cover for a blood pressure measurement device according to claim 1, wherein the bag body has a width in a lateral direction that is formed to be greater than a width of the curler in a lateral direction.

* * * * *